US012611129B2

(12) United States Patent
Kayser et al.

(10) Patent No.: US 12,611,129 B2
(45) Date of Patent: Apr. 28, 2026

(54) ANTICIPATING PATIENT NEEDS ASSOCIATED WITH TOILETING

(71) Applicant: Hill-Rom Services, Inc., Batesville, IN (US)

(72) Inventors: Susan A. Kayser, Batesville, IN (US); Sinan Batman, Cary, NC (US); Jennifer Marie Rizzo, Guilford, IN (US); Dee Anna Kumpar, Freeland, MI (US); Jie Zhou, Batesville, IN (US); Michael S. Hood, Batesville, IN (US); Lori A. Zapfe, Milroy, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 1114 days.

(21) Appl. No.: 17/669,926

(22) Filed: Feb. 11, 2022

(65) Prior Publication Data
US 2022/0257163 A1 Aug. 18, 2022

Related U.S. Application Data

(60) Provisional application No. 63/149,156, filed on Feb. 12, 2021.

(51) Int. Cl.
*A61B 5/20* (2006.01)
*A61B 5/00* (2006.01)
*G16H 10/60* (2018.01)

(52) U.S. Cl.
CPC .............. *A61B 5/20* (2013.01); *A61B 5/4836* (2013.01); *A61B 5/7267* (2013.01);
(Continued)

(58) Field of Classification Search
CPC ....... A61B 5/20; A61B 5/4836; A61B 5/7267; A61B 5/7282; A61B 5/747; A61B 5/0022;
(Continued)

(56) References Cited

U.S. PATENT DOCUMENTS 9,098,993 B2 8/2015 Reed, Jr.
9,107,776 B2 8/2015 Bergman et al.
(Continued)

FOREIGN PATENT DOCUMENTS

CN 105125348 A 12/2015

*Primary Examiner* — Quan Zhen Wang
*Assistant Examiner* — Rajsheed O Black-Childress
(74) *Attorney, Agent, or Firm* — Lee & Hayes, P.C.

(57) ABSTRACT
This disclosure is directed towards a patient management system for anticipating patient needs associated with toileting. In some examples, a computing device of the patient management system determines a toilet need schedule for a patient based on conditions of the patient (e.g., from an electronic medical record of the patient) and/or events that occur associated with the patient, such as meals or beverages consumed, toileting events, medications taken, and so forth. Additionally, the patient management system may sense when a patient is moving towards a patient relief device, when the patient is using the patient relief device, and/or when the patient has concluded using the patient relief device. Such information may be provided to a healthcare provider so that the healthcare provider may assist with toileting needs to increase safety of the patient and/or to reduce accidents associated with toileting needs of the patient.

18 Claims, 7 Drawing Sheets

(52) U.S. Cl.
CPC ............ *A61B 5/7282* (2013.01); *A61B 5/747*
(2013.01); *G16H 10/60* (2018.01)

(58) Field of Classification Search
CPC ... A61B 5/1113; A61B 5/1115; A61B 5/6889;
A61B 5/1128; G16H 10/60; G16H 15/00;
G16H 20/10; G16H 40/63; G16H 40/67;
G16H 50/20; G16H 50/70; G16H 80/00
See application file for complete search history.

(56)                    References Cited

U.S. PATENT DOCUMENTS

| | | | |
|---|---|---|---|
| 9,931,252 B2 | 4/2018 | Carney et al. | |
| 9,978,244 B2 | 5/2018 | Ribble et al. | |
| 10,147,298 B2 | 12/2018 | Ten Kate | |
| 10,172,522 B2 | 1/2019 | Ribble | |
| 10,646,171 B2 | 5/2020 | Brasch et al. | |
| 10,685,249 B2 * | 6/2020 | Zyglowicz ............. | G16H 40/63 |
| 10,692,347 B2 | 6/2020 | Yang | |
| 10,722,146 B2 | 7/2020 | Kilcran et al. | |
| 2013/0023786 A1 * | 1/2013 | Mani ....................... | A61F 13/42 |
| | | | 600/561 |
| 2013/0332184 A1 * | 12/2013 | Burnham ............... | G16H 40/63 |
| | | | 705/2 |
| 2016/0175164 A1 * | 6/2016 | Mashin-Chi ........... | G06N 3/126 |
| | | | 702/19 |
| 2018/0075725 A1 | 3/2018 | Geng et al. | |
| 2019/0254582 A1 | 8/2019 | Wei et al. | |
| 2019/0336065 A1 | 11/2019 | Ricciardi et al. | |

\* cited by examiner

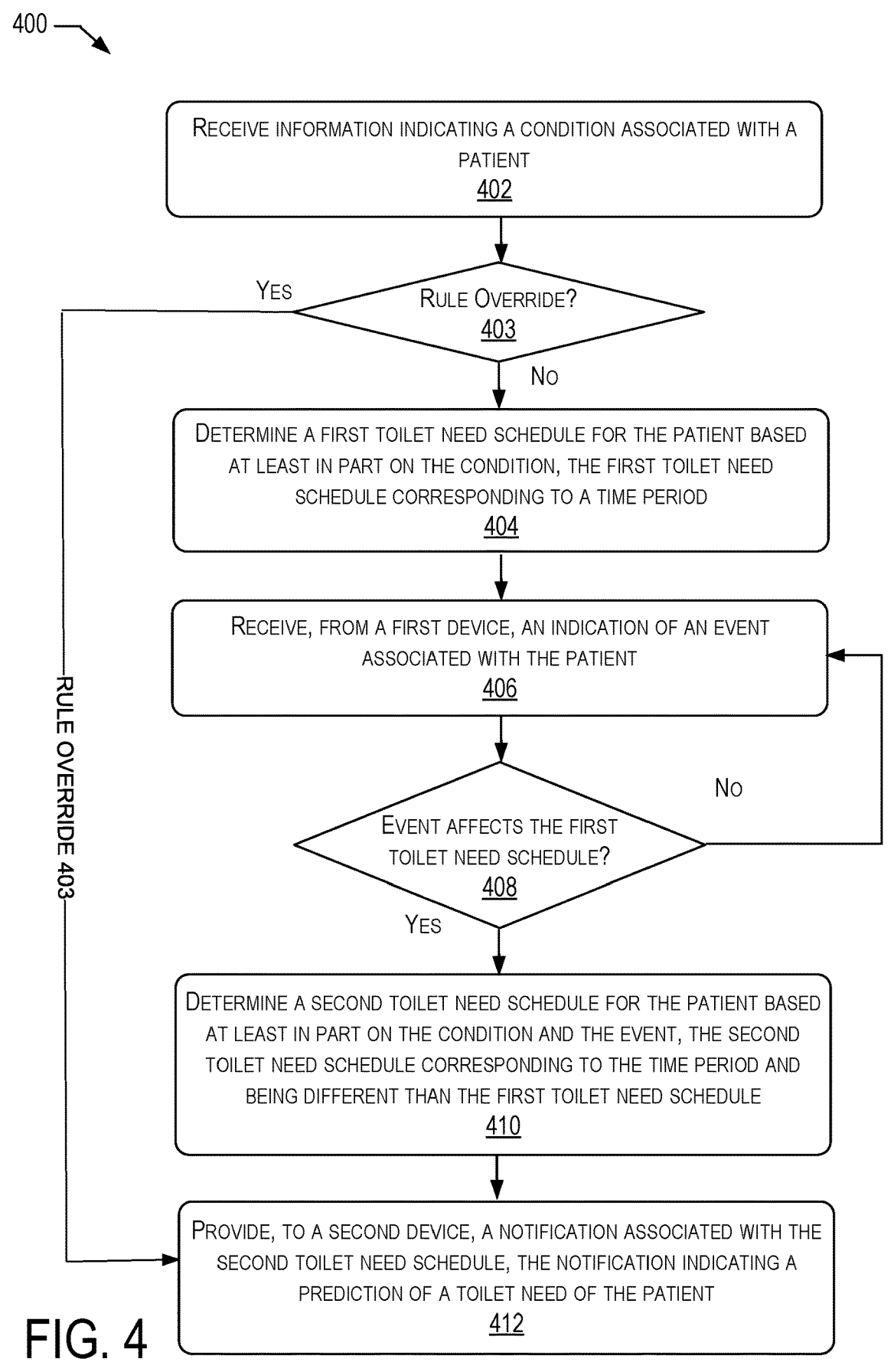

400 —

RECEIVE INFORMATION INDICATING A CONDITION ASSOCIATED WITH A
PATIENT
402

YES ◄ RULE OVERRIDE?
403
No

DETERMINE A FIRST TOILET NEED SCHEDULE FOR THE PATIENT BASED
AT LEAST IN PART ON THE CONDITION, THE FIRST TOILET NEED
SCHEDULE CORRESPONDING TO A TIME PERIOD
404

RECEIVE, FROM A FIRST DEVICE, AN INDICATION OF AN EVENT
ASSOCIATED WITH THE PATIENT
406

EVENT AFFECTS THE FIRST
TOILET NEED SCHEDULE?     No
408
YES

RULE OVERRIDE 403

DETERMINE A SECOND TOILET NEED SCHEDULE FOR THE PATIENT BASED
AT LEAST IN PART ON THE CONDITION AND THE EVENT, THE SECOND
TOILET NEED SCHEDULE CORRESPONDING TO THE TIME PERIOD AND
BEING DIFFERENT THAN THE FIRST TOILET NEED SCHEDULE
410

PROVIDE, TO A SECOND DEVICE, A NOTIFICATION ASSOCIATED WITH THE
SECOND TOILET NEED SCHEDULE, THE NOTIFICATION INDICATING A
PREDICTION OF A TOILET NEED OF THE PATIENT
412

FIG. 4

600 ——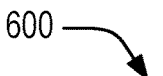

RECEIVE, FROM A SENSING DEVICE ASSOCIATED WITH A PATIENT RELIEF
DEVICE, FIRST SENSOR DATA
602

PATIENT USING THE
PATIENT RELIEF DEVICE?          No
604

YES

RECEIVE, FROM THE SENSING DEVICE ASSOCIATED WITH THE PATIENT
RELIEF DEVICE, SECOND SENSOR DATA
606

PATIENT CONCLUDED USING
THE PATIENT RELIEF DEVICE?          No
608

YES

PROVIDE A NOTIFICATION TO A DEVICE ASSOCIATED WITH A HEALTHCARE
PROVIDER, THE NOTIFICATION INDICATING THAT THE PATIENT HAS
CONCLUDED USING THE PATIENT RELIEF DEVICE
610

ANTICIPATING PATIENT NEEDS ASSOCIATED WITH TOILETING

CROSS-REFERENCE TO RELATED APPLICATIONS

This application is a Nonprovisional of and claims priority to U.S. Provisional Patent Application No. 63/149,156, filed on Feb. 12, 2021, the entire disclosure of which is hereby incorporated herein by reference.

TECHNICAL FIELD

This application is directed to a patient management system, and in particular, to a system configured to anticipate patient needs associated with toileting and notifications that may stem from those toileting needs.

BACKGROUND

Toileting is a significant consideration when caring for patients in a hospital setting. In many cases, patients require at least some assistance from healthcare providers with toileting needs, including tasks such as catheter maintenance and removal, moving to a patient relief device (e.g., a toilet or a commode) from a hospital bed or chair, returning from the patient relief device to the hospital bed or chair, and/or cleaning and sanitizing following a toileting event. Healthcare providers using conventional patient management systems rely on a patient to call for the healthcare provider prior to a toileting event, and/or a standard rounds schedule to check on patients that does not take individual patient toileting needs into account. Such conventional patient management systems often do not leave sufficient time for the healthcare provider to reach the patient before a toileting event occurs, leaving the patient at risk of a fall or an accident. Similarly, such conventional patient management systems do not provide mechanisms for alerting healthcare providers when a toileting event concludes, leaving the patient at risk of a fall, an accident, or in some cases infection if cleaning and sanitizing are delayed.

The various example embodiments of the present disclosure are directed toward overcoming one or more of the deficiencies associated with patient management systems.

SUMMARY

Broadly, the systems and methods disclosed and contemplated herein are directed towards a patient management system for anticipating patient needs associated with toileting. In some examples, a computing device of the patient management system receives information indicating a condition associated with a patient. The computing device receives, from a first device, an indication of an event associated with the patient. Using a machine-learned model, the computing device determines a first toilet need schedule for the patient based at least in part on the condition and the event, where the first toilet need schedule corresponds to a time period. The computing device may also provide, to a second device, a notification associated with the first toilet need schedule, where the notification indicates a prediction of a toilet need of the patient.

In some examples, a method trains a machine learning model to identify relationships between patient conditions and patient preferences. The method receives information indicating a condition associated with a patient. The method receives information indicating one or more preferences of the patient associated with toileting events. The method then determines, by the trained machine-learned model, a first toilet need schedule for the patient based at least in part on the condition and the one or more preferences, the first toilet need schedule corresponding to a time period. The method then provides to an electronic device, a notification associated with the first toilet need schedule, the notification indicating a prediction of a toilet need of the patient.

In some examples, a system comprises of a processor, a first electronic device, a sensor, and one or more computer-readable media storing instructions. The instructions perform a step of receiving first information from the first electronic device, via the network, indicating a condition associated with a patient. The instructions perform another step of receiving second information from the sensor indicating an event associated with the patient. The instructions perform another step of determining, by a machine-learned model, a first toilet need schedule for the patient based at least in part on the first information and the second information, the first toilet need schedule corresponding to a time period. The instructions additionally perform another step of generating, based on the first toilet need schedule, a notification indicating a predicted toilet need of the patient. The instructions also perform a step of providing the notification to a second electronic device via the network.

BRIEF DESCRIPTION OF THE DRAWINGS

FIG. 4 is an example process for determining and updating a toilet need schedule, according to the techniques described herein.

FIG. 6 is an example process for providing advance notice of toileting events, according to the techniques described herein.

DETAILED DESCRIPTION

Figure 1:
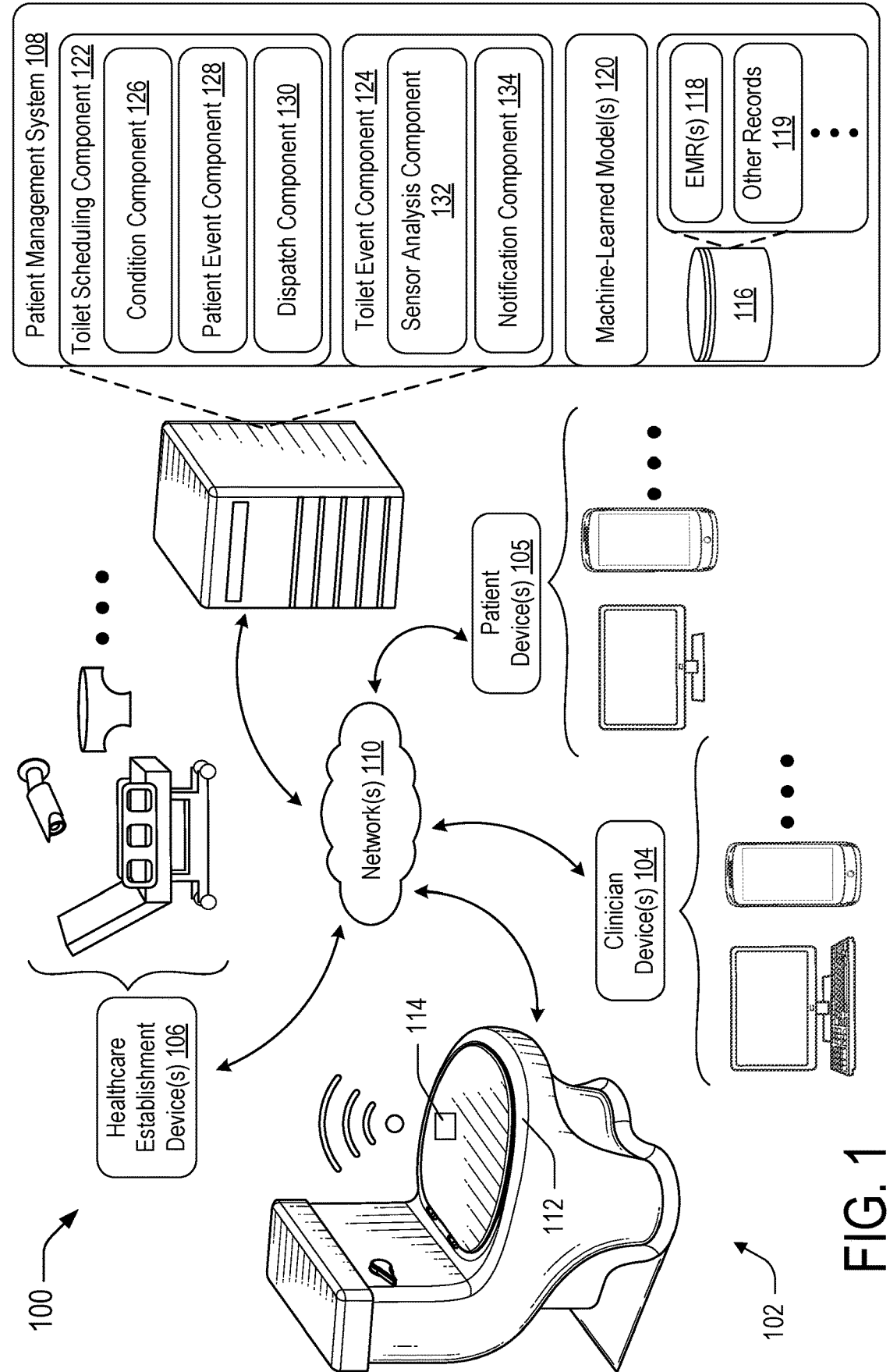
FIG. 1 shows a schematic block diagram of an example patient management system environment, in accordance with examples of the disclosure.

Various embodiments of the present disclosure will be described in detail with reference to the drawings, wherein like reference numerals represent like parts and assemblies throughout the several views. Additionally, any examples set forth in this specification are not intended to be limiting and merely set forth some of the many possible embodiments.

FIG. 1 shows a schematic block diagram of an example patient management system environment 100. The example patient management system environment 100 includes a patient relief device 102, one or more clinician devices 104, one or more patient devices 105, one or more healthcare establishment devices 106, and a patient management system 108. The patient relief device 102, the clinician devices 104, the healthcare establishment devices 106, and/or the patient management system 108 may be in communication via one or more networks 110.

In some examples, the patient relief device 102 may be a toilet, a commode, a catheter, a toilet paper roll, and/or other type of device configured to be used in association with a toilet event. As used herein, a toilet event may include events such as urination, bowel movements, and so forth. In at least some examples, the patient relief device 102 includes one or more sensors 112 and one or more transmitters 114. For instance, the sensors 112 included in the patient relief device 102 may include a pressure sensor associated with a seat of the patient relief device 102, where the pressure sensor is configured to detect pressure applied to the seat of the patient relief device. The sensors 112 may include a motion sensor (e.g., an accelerometer, an inertial measurement unit (IMU), a gyroscope, etc.), where the motion sensor may detect motion associated with a toilet paper roll, motion associated with the patient (e.g., the patient exiting a bed or chair, the patient fidgeting, the patient moving across a hospital room, etc.), motion of the seat of the toilet, and so forth.

Alternatively or additionally, the sensors 112 may include one or more microphones and/or microphone arrays. For instance, the sensors 112 may include one or more directional microphones, one or more omnidirectional microphones, and the like. In an illustrative example, a sensor 112 may be a directional microphone associated with a region near the seat of the patient relief device 102 and configured to detect sound associated with a person sitting on the patient relief device 102, flushing the patient relief device 102, and so on. In another illustrative example, a sensor 112 may be a directional microphone associated with a region near a sink in a bathroom and configured to detect sound associated with a person washing their hands in the sink. In yet another illustrative example, a sensor 112 may be an omnidirectional microphone associated with a bathroom and configured to detect various types of sounds in the bathroom and origi-nating from different locations within the bathroom.

The sensors 112 may include a radar sensor configured to determine a position of a person in a bathroom or hospital room, such as relative to the patient relief device 102. For example, a sensor 112 may be a radar sensor located on a back of the patient relief device 102 and be configured to detect whether a person is standing proximate to or sitting on the patient relief device 102.

In some cases, the sensors 112 may include a heart rate sensor configured to detect a heartrate when contact is present between a person and a seat of the patient relief device 102 (e.g., when the patient sits on the seat). For instance, the sensors 112 may include one or more of a single-lead electrocardiogram (ECG) sensor to measure electrical activity of the heart, a photoplethysmogram (PPG) sensor to measure blood oxygenation and localized pulse timing, a ballistocardiogram (BCG) sensor to measure mechanical forces associated with a cardiac cycle, and so forth. The sensors 112 may also include a respiration sensor configured to detect respiration when contact is administered between a person and the seat of the patient relief device 102. A respiration sensor may take a variety of forms, such as a BCG sensor, an infrared camera configured to detect changing oxygen levels of a patient, a microphone to detect breathing sounds, a microphone array in combination with a camera to detect a location of a mouth or nose of the patient and direct the microphone array to detect breathing sounds at the location of the mouth or nose, and so forth.

In some examples, the sensors 112 may include a camera or other type of light beam sensor, such as an infrared sensor.

In some cases, a camera may capture images or video that may indicate the presence of a person using the patient relief device 102, where the camera may be located on the patient relief device 102 to ensure privacy (e.g., by capturing images or video of a person's feet proximate the patient relief device). Similarly, a light beam sensor such as an infrared sensor may be configured to determine presence of a person using the patient relief device 102 when the light beam is interrupted on a path to a receiver by a person using the patient relief device 102.

In examples, the clinician devices 104 may include com-puting devices such as mobile phones, tablet computers, laptop computers, desktop computers, and the like. The clinician devices 104 may provide a clinician (e.g., a phy-sician, nurse, technician, pharmacist, dentist, etc.) with information about the health of the patient. In some cases, the clinician devices 104 may exist within a healthcare provider establishment (e.g., alongside the patient relief device 102 and/or the healthcare establishment devices 106), although examples are also considered in which the clinician devices 104 exist and/or are transported outside of a health-care provider establishment, such as a physician's mobile phone or home desktop computer that the physician may use when the physician is on-call. In at least some examples, the clinician devices 104 may be configured to display toilet need schedules and provide notifications associated there-with received from the patient management system 108, and/or provide notifications received from the patient man-agement system 108 related to a sensed toileting event (e.g., outside of a toilet need schedule).

In examples, the patient devices 105 may include com-puting devices such as mobile phones, tablet computers, laptop computers, desktop computers, and the like. The patient devices 105 may provide a patient or someone who has a relationship with a patient (e.g., family member, friend, caregiver, etc.) the ability to notify and otherwise be in contact with at least a clinician. In some cases, the patient devices 105 may exist within a healthcare provider estab-lishment (e.g., alongside the patient relief device 102, the clinician devices 104, and/or the healthcare establishment devices 106), although examples are also considered in which the patient devices 105 exist and/or are transported outside of a healthcare provider establishment, such as a patient's personal mobile phone or home desktop computer that the patient may use to connect to the healthcare provider establishment. In at least some examples, the patient devices 105 may be configured to run specialized software applica-tions (e.g., the Voalte Experience™) that may allow patients to notify clinicians that they are in need of a toileting event or communicate to such clinicians that a toileting event has already occurred.

In some examples, the healthcare establishment devices 106 may include devices that generally exist in a healthcare establishment (e.g., physician's office, hospital, clinic, den-tist's office, pharmacy, ambulance, and the like) that may impact and/or monitor the health of the patient. For instance, the healthcare establishment devices 106 may include cam-eras, microphones, radar sensors, heat sensors, light beam sensors, pressure sensors (e.g., in a floor), mobility devices (e.g., an overhead lift, a walker, etc.), items worn by a patient (such as a diaper, a sock, a gown, etc.), blood pressure devices, $SpO_2$ devices, temperature devices, respi-ratory devices, ECG devices, beds and other furniture, and so on. While the healthcare establishment devices 106 are described as existing within a healthcare establishment, examples are considered in which such devices may be found outside of a healthcare establishment, in some cases.

The patient relief device 102, the clinician devices 104, and/or the healthcare establishment devices 106, may include a processor, microprocessor, and/or other computing device components, shown and described below. For instance, the patient relief device 102, the clinician devices 104, and/or the healthcare establishment devices 106 may be configured as mobile phones, tablet computers, laptop computers, etc., to deliver or communicate patient data, sensor data, notifications, and the like amongst one another and to other devices. The transmitter 114 included in the patient relief device 102 may be configured to receive electronic signals from the sensors 112 and distribute information corresponding to the electronic signals, via the networks 110, to the clinician devices 104, the healthcare establishment devices 106, and/or the patient management system 108. Though not explicitly pictured, the clinician devices 104, the healthcare establishment devices 106, and/or the patient management system 108 may include transmitters as well.

The network 110 is typically any type of wireless network or other communication network known in the art. Examples of the network 110 include the Internet, an intranet, a wide area network (WAN), a local area network (LAN), and a virtual private network (VPN), cellular network connections and connections made using protocols such as 802.11a, b, g, n and/or ac. Alternatively or additionally, the network 114 may include a nanoscale network, a near-field communication network, a body-area network (BAN), a personal-area network (PAN), a near-me area network (NAN), a campus-area network (CAN), and/or an inter-area network (IAN). In some cases, more than one network 110 may be used to transfer data throughout the example system 100. In an illustrative example, a hospital room may include a PAN that enables the patient relief device 102, the clinician devices 104 (if present in the hospital room), and the healthcare establishment devices 106 associated with the hospital room to collect data at a single location, such as at the patient relief device 102. The transmitter 114 of the patient relief device 112 may provide the data once collected from the various devices included in the hospital room to the patient management system 108, such as via a LAN.

The patient management system 108 may be comprised of one or more server computing devices, which may communicate with the patient relief device 102, the clinician devices 104, and/or the healthcare establishment devices 106 to respond to queries, receive data, and so forth. Communication between the patient management system 108, the patient relief device 102, the clinician devices 104, and/or the healthcare establishment devices 106 occurs via the network 110, where the communication can include data collected by the sensors 112 and transmitted via the transmitter 114, notifications distributed to the clinician devices 104 regarding toilet events and/or toilet need schedules, and so forth. A server of the patient management system 108 can act on these requests from the patient relief device 102, the clinician devices 104, and/or the healthcare establishment devices 106, determine one or more responses to those queries, and respond back to the patient relief device 102, the clinician devices 104, and/or the healthcare establishment devices 106. A server of the patient management system 108 may also include one or more processors, microprocessors, or other computing devices as discussed in more detail in relation to FIG. 7.

The patient management system 108 may include one or more database systems 116 (also referred to herein as simply a "database 116") accessible by a server storing different types of information. For instance, the database 116 can store correlations and algorithms used to manage patient data, such as electronic medical records (EMRs) 118 associated with one or more patients. The database 116 may store other records 119 as well, which may be associated with a patient but may not be otherwise included in the EMR 118. For example, the other records 119 may include medication administration records (MARs), records of adverse events involving the patient, and so forth. Additionally, in some instances, the database 116 may store correlations and algorithms to manage events associated with patients and/or healthcare providers received from the patient relief device 102, the clinician devices 104, and/or the healthcare establishment devices 106. The database 116 may reside on a server of the patient management system 108 or on separate computing device(s) accessible by the patient management system 108.

Additionally, in some examples, the patient management system 108 may include one or more machine-learned models 120. While shown as being included with the patient management system 108 in the example system 100, examples are considered in which any or all of the patient relief device 102, the clinician devices 104, the patient devices 105, or the healthcare establishment devices 106 include the machine-learned models to utilize in performing the functionality described herein. In some instances, the patient management system 108 may input at least a portion of the EMR 118 associated with a patient indicating one or more conditions into the machine-learned model(s) 120. Alternatively or additionally, the patient management system 108 may receive sensor data from one or more of the patient relief device 102, the clinician device 104, or the healthcare establishment device 106, and input at least a portion of this data into the machine-learned model(s) 120.

In some cases, the machine-learned models 120 may comprise a regression model, configured to output a time or times at which a patient is likely to experience a toileting need, a time or times at which a healthcare provider should check on a toileting need of the patient, and other predictions which may utilize as input any of the sources of data and/or devices described in this disclosure but is not limited by such data and/or devices. For instance, the machine-learned model 120 may be configured to provide a prediction of a toileting need that is customized to the patient based on one or more conditions indicated in the EMR 118 associated with the patient, and/or one or more events associated with the patient. As used herein, an "event" refers to an event that may have an effect on a toileting need of a patient, such as a meal eaten by the patient, a feeding administered to the patient via a feeding tube, a beverage consumed by the patient, a medication administered to the patient, an instance of a toileting event by the patient, a preference of the patient associated with toileting events, an so forth. A preference of the patient may refer to a frequency at which the patient executes toileting events, such as once per hour, once every two hours, and so on. Alternatively or additionally, a preference of the patient may refer to an urgency at which the patient executes toileting events. To illustrate, some patients may express a need for a toileting event 30 minutes before a toilet event accident, and other patients may express a need for a toileting event 5 minutes before a toilet event accident.

In some examples, the machine-learned models 120 may comprise one or more supervised models (e.g., classification, regression, similarity, or other type of model), unsupervised models (e.g., clustering, neural network, or other type of model), and/or semi-supervised models configured to anticipate patient needs associated with toileting. In at least some cases, the patient management system 108 may utilize one or more supervised models (e.g., classification, regression, similarity, or other type of model), unsupervised models (e.g., clustering, neural network, or other type of model), and/or semi-supervised models to determine probabilities for preferences of a particular patient associated with frequency and/or urgency for toileting events. Alternatively or additionally, the machine-learned models 120 may include retrospective, descriptive, predictive, and/or prescriptive models which may be used to implement the functionality described herein. Types of machine-learned models that the patient management system 108 may employ to provide toilet need schedules customized to a patient, a healthcare provider, and/or a healthcare establishment may include subject fixed-effect models and subject random-effect models, although other types of models are also considered.

In some examples, the patient management system 108, patient relief device 102, the clinician devices 104, the patient devices 105, and/or the healthcare establishment devices 106 may generate, store, and/or selectively share patient data between one another to provide a patient and/or healthcare providers with improved outcomes by effectively anticipating toileting needs and communicating information about such toileting needs. For example, the patient management system 108 may include a toilet scheduling component 122 that is configured to determine a toilet need schedule for one or more patients and provide the toilet need schedule to healthcare providers as appropriate. In some instances, the patient management system 108 includes a toilet event component 124 configured to detect a patient moving towards (or attempting to move towards) the patient relief device 102, detect that the patient is using the patient relief device 102, and/or detect that the patient has concluded using the patient relief device 102, along with providing notifications to healthcare providers to assist with toileting needs of the patient as appropriate. Example configurations of the patient relief device 102, the clinician devices 104, the healthcare establishment devices 106, and/or the patient management system 108 and methods for their use, are shown and described with continued reference to FIG. 1, and with reference to at least FIGS. 2-8 below.

Toilet Scheduling

As mentioned above, the toilet scheduling component 122 is configured to determine a toilet need schedule for one or more patients and provide the toilet need schedule to healthcare providers as appropriate. As shown, the toilet scheduling component 122 may include a condition component 126, a patient event component 128, and a dispatch component 130. In at least some examples, the condition component 126, the patient event component 128, and the dispatch component 130 provide functionality to anticipate patient needs associated with toileting by determining toilet need schedules for patients and providing the toilet need schedules to one or more healthcare providers to assist with toileting events as anticipated by the toilet need schedules.

In some examples, the condition component 126 receives information indicating a condition associated with a patient, such as from an EMR 118 stored in the database 116. In some instances, conditions associated with a patient may have an effect on toileting needs of the patient. For example, a condition associated with a patient may cause the patient to have toileting events more or less frequently than traditional nursing rounds in a hospital. Conditions that the condition component 126 may determine from the EMR 118 may include, but are not limited to, a medication administered to the patient that affects a frequency of urine output or bowel movements, an intravenous (IV) fluid dosage administered to the patient, a disease of the patient, a pregnancy of the patient, a demographic of the patient, an age of the patient, a body mass index (BMI) of the patient, a presence of a catheter on the patient, a presence of an incontinence management device (e.g., a diaper) on the patient, a colostomy or an ostomy on the patient, mobility of the patient, and so forth. Medications that may affect frequency of urine output or bowel movements may include, for instance, Lasix®, diuretics, stool softeners, and the like. Diseases of the patient that may affect frequency of urine output or bowel movements may include, for example, urinary tract infections (UTIs), chronic obstructive pulmonary disease (COPD), edema, nephrology, benign prostatic hyperplasia, diabetes, a clostridium difficile (C-diff) infection, anuria, and so on.

Additionally, in some cases, the EMR 118 may include a preference of the patient associated with toileting events. As mentioned above, a preference of the patient may refer to a frequency at which the patient executes toileting events, and/or an urgency at which the patient executes toileting events. The preference of the patient may be provided by the patient themselves, and/or by a healthcare provider caring for the patient such as via an input using the clinician device 104.

After receiving one or more conditions associated with the patient, the condition component 126 determines a first toilet need schedule for the patient based at least in part on the condition. The first toilet need schedule may correspond to a time period, where the time period may be a fixed time period or a variable time period. For example, a fixed time period corresponding to the first toilet need schedule may be associated with an 8-hour or a 12-hour shift for a healthcare provider (e.g., a nurse) who is assigned to care for the patient, and the first toilet need schedule may predict a number of toileting events to occur during the fixed time periods and times at which such predicted toileting events will occur. A variable time period corresponding to the first toilet need schedule may be associated with a time at which a next toileting event is predicted to occur based on the condition(s) of the patient, such as by providing a countdown to a predicted next toileting event.

To determine the first toilet need schedule, the condition component 126 may employ one or more rules-based algorithms, and/or the machine-learned models 120. For instance, the condition component 126 may input the condition associated with the patient into the machine-learned model 120, and receive a prediction of a time at which the patient will experience a toileting need from the machine-learned model 120. The condition component 126 may use the prediction of the time at which the patient will experience the toileting need to determine the first toilet need schedule. In an illustrative example, the condition component 126 may provide a countdown timer to the clinician device 104 to the predicted time at which the patient will experience the toileting need. Alternatively or additionally, the condition component 126 may provide the first toilet need schedule (e.g., a fixed 12-hour schedule) to the clinician device that includes an indication of the predicted time at which the patient will experience the toileting need. As described above, the machine-learned model 120 may be a regression model, such as a subject fixed-effect model and/or a subject random-effect model, configured to determine the first toilet need schedule specific to the patient and based on the one or more conditions input to the model.

In some examples, the condition component 126 determines the first toilet need schedule based at least in part on patient mobility, such as an amount of time and/or an amount of assistance needed to get the patient from a hospital bed to the patient relief device 102. For example, a first patient that is capable of independently exiting and ambulating from a hospital bed to the patient relief device 102 requires less time and assistance to reach the patient relief device 102 than a second patient that needs multiple healthcare providers and an overhead lift to exit the hospital bed, along with multiple healthcare providers to move the patient from the hospital bed to the patient relief device 102. Accordingly, the condition component 126 may receive an indication of a mobility of the patient as the condition associated with the patient, and use the mobility to generate the first toilet need schedule to account for the patient's mobility. In the case of the first patient just described, the condition component 126 may generate the first toilet need schedule to send a healthcare provider to the patient's hospital room five minutes prior to a time of an anticipated toileting need to ask if the patient would like assistance with toileting. In the case of the second patient just described, the condition component 126 may generate the first toilet need schedule to send two healthcare providers to the patient's hospital room fifteen minutes prior to a time of an antici-pated toileting need to begin moving the patient to the toilet, including using the overhead lift. In at least some examples, the condition component 126 may input the condition indicative of the mobility of the patient into the machine-learned model 120 and receive a time at which to send one or more healthcare providers to the hospital room of the patient based on the mobility of the patient, and include this time in the first toilet need schedule.

Examples are also considered in which the condition component 126 determines the first toilet need schedule using one or more rules-based algorithms. In an illustrative example, the condition component 126 may determine that the condition is associated with a presence of a catheter on the patient. Rather than employing the machine-learned model 120 in this instance, the condition component 126 may leverage a rules-based algorithm for patients with catheters, to generate the first toilet need schedule with a reminder to check a status of the catheter and/or to remove the catheter. By selectively employing a rules-based algo-rithm in place of a machine-learned model based on a condition of the patient, the condition component 126 may reduce processing resources of a computing device when a machine-learned model is not necessary for effective patient care.

In some examples, the dispatch component 130 provides a notification associated with the first toilet need schedule to one or more of the clinician devices 104 via the network 110. As mentioned above, the first toilet need schedule may comprise a fixed time period, such as a shift duration of a healthcare provider. In such cases, the dispatch component 130 may provide the first toilet need schedule associated with the fixed time period, including predicted times at which the patient will have a toileting need, to the clinician device 104. In this way, a healthcare provider that receives the first toilet need schedule associated with the fixed time period at the clinician device 104 may view upcoming predicted toileting needs of the patient, and execute tasks accordingly.

Alternatively or additionally as described above, the first toilet need schedule may comprise a variable time period, such as a countdown to a next predicted toileting need of the patient. In such cases, the dispatch component 130 may determine a clinician device 104 associated with a particular healthcare provider to provide the notification associated with the first toilet need schedule to, such as based on a location of the clinician device 104 (e.g., in cases where the clinician device 104 is a mobile device carried by a health-care provider) relative to the patient, a task being performed by the healthcare provider associated with the clinician device 104, and the like. Therefore, the dispatch component 130 may dynamically direct healthcare providers to patients predicted to have upcoming toileting needs based on loca-tion and/or availability of the healthcare providers.

In some examples, the dispatch component 130 may utilize the machine-learned models 120 to determine toilet need schedules and/or provide notifications related to dis-patching healthcare providers to one or more patients to assist with toileting events. For instance, different hospital wards may have different protocols for healthcare providers that may affect how the healthcare providers respond to toileting events, such as questions to ask each patient when visiting a room, charting events associated with patients, and the like. Accordingly, the patient management system 108 may store one or more parameters associated with individual hospital ward protocols in the database 116. Prior to pro-viding a notification associated with the first toilet need schedule to the clinician device 104, the dispatch component 130 may input the one or more parameters associated with the individual hospital ward protocols and the first toilet need schedule into the machine-learned model 120. The dispatch component 130 may receive a time at which to direct the healthcare provider to assist the patient with a toileting need from the machine-learned model 120, which accounts for the parameters associated with the individual hospital ward protocol and the condition of the patient determined from the EMR 118.

In some examples, the dispatch component 130 may use the first toilet need schedule to determine a number of healthcare providers to staff for a shift. For instance, the dispatch component 130 may determine, based in part on the first toilet need schedule for a patient, a predicted number of toilet need events over a future time period (such as an upcoming shift). The dispatch component 130 may similarly determine predicted numbers of toilet need events over the future time period for other patients in a hospital ward. In at least some examples, the dispatch component 130 deter-mines a number of healthcare providers to staff over the future time period based on the predicted number. Addition-ally, in some cases, the dispatch component 130 may deter-mine one or more types of healthcare providers to staff over the future time period as well. The dispatch component 130 may update the predicted number of toilet need events as events associated with patients occur prior to the future time period, and/or during the time period (e.g., to call in addi-tional healthcare providers in a middle of a shift when needed).

In an illustrative example, the dispatch component 130 may determine that there are 12 patients in a ward for an upcoming shift, and that 6 total toilet need events are predicted each hour between all 12 of the patients in the ward. In this example, the dispatch component 130 may determine that to accommodate the 6 predicted toilet need events per hour, that 3 healthcare providers should be staffed for the shift. Further in the illustrative example, the dispatch component 130 may determine that two catheter removals are predicted during the shift, and thus may staff at least two registered nurses having qualifications to remove catheters as two of the 6 healthcare providers staffed for the shift. In at least some examples, the dispatch component 130 may provide notifications to clinician devices 104 associated with healthcare providers who are staffed during the shift indi-cating that the healthcare providers are staffed. Alternatively or additionally, the dispatch component 130 may provide notifications to clinician devices 104 associated with healthcare providers who are not staffed during the shift indicating that the healthcare providers are not staffed and thus do not need to come to work for that shift.

Additionally, in many cases healthcare providers are assigned to more than one patient during a shift, and when a particular healthcare provider has multiple demanding patients (related to toileting needs or otherwise), the healthcare provider may not be able to provide the desired level of care to each patient. Accordingly, the dispatch component 130 may assign patients to a healthcare provider during a shift to balance workloads of the healthcare providers based on predicted toileting needs of the patients. Similar to the discussion above, the dispatch component 130 may determine, based in part on the first toilet need schedule for a patient, a predicted number of toilet need events over a future time period (such as an upcoming shift). The dispatch component 130 may similarly determine predicted numbers of toilet need events over the future time period for other patients in a hospital ward. The dispatch component 130 may also assign the patient associated with the first toilet need schedule to a particular healthcare provider for the future time period based on the predicted number of toilet need events during the first toilet need schedule. For example, the dispatch component 130 may assign the patient to the particular healthcare provider based on times and/or durations of predicted toileting needs such that the healthcare provider does not have more than three predicted toilet need events per hour between the healthcare provider's assigned patients.

In some examples, the patient event component 128 of the toilet scheduling component 122 receives an indication of an event associated with the patient. The patient event component 128 may receive the indication of the event from the patient relief device 102, the clinician device 104, and/or the healthcare establishment device 106. As described above, an "event" refers to an event that may have an effect on a toileting need of a patient, such as a meal eaten by the patient, a feeding administered to the patient via a feeding tube, a beverage consumed by the patient, a medication administered to the patient, an instance of a toileting event by the patient, a preference of the patient associated with toileting events, and so forth. The patient event component 128 determines a second toilet need schedule for the patient based at least in part on the condition and the event.

In at least some examples, the second toilet need schedule corresponds to the time period associated with the first toilet need schedule, but may be different from the first toilet need schedule due to the occurrence of the event. For instance, the first toilet need schedule may correspond to a fixed time period such as a shift of one or more healthcare providers, as described herein. The first toilet need schedule, based at least in part on the condition of the patient, may include a time at which a predicted toilet need will occur. When an event such as administration of a medication or consuming a meal occurs, the event may impact the time at which the predicted toilet need will occur. Accordingly, the patient event component 128 updates a toilet need schedule of a patient based on events that occur related to the patient so that the healthcare providers can provide care that is needed and avoid unnecessary visits when toileting events are unlikely.

For instance, consider the illustrative example above in which the condition component 126 determines the first toilet need schedule for a patient having a catheter, where the first toilet need schedule includes a catheter removal reminder. The patient event component 128 may receive an indication of an event in which the catheter is removed from the patient, such as from the clinician device 104 associated with the healthcare provider that removed the catheter. In response to this event, the patient event component 128 determines the second toilet need schedule to resume toilet need events related to urination, such as every two hours. The patient event component 128 may provide the dispatch component 130 with the second toilet need schedule, and the dispatch component 130 may provide notifications to a clinician device 104 associated with a healthcare provider to assist with toilet needs related to the urination toilet need schedule.

Different types of events may cause a duration between toilet needs to change. For example, food and/or beverage consumption may increase or decrease a time period between toilet need events. In an illustrative example, the first toilet need schedule may be characterized by a predicted toilet need every two hours, based on conditions in the EMR 118 of the patient, and may supply notifications to the clinician device 104 according to the predicted toilet need. During the patient's hospital stay, the patient may consume a beverage, such as 8 ounces of water, which a healthcare provider may document as an event using the clinician device 104. Upon receiving an indication of the event, the patient event component 128 may decrease the two hour time period until a next predicted toilet need to 90 minutes, and may cause the second toilet need schedule to be characterized by the updated predicted toilet need. The patient event component 128 may provide a notification to the clinician device 104 associated with the healthcare provider so that the healthcare provider is present for the toileting need of the second toilet need schedule. In this way, the toilet scheduling component 122 anticipates toileting needs of the patient and notifies the healthcare provider accordingly, thus reducing the likelihood of accidents or injuries of the patient related to toileting events.

Toilet events by a patient may affect a toilet need schedule as well. For instance, some toilet events may fall outside of predictions of the toilet need schedule. The patient event component 128 may receive an indication of an event, where the event comprises a toileting event, from the patient relief device 102, the clinician device 104, and/or one or more of the healthcare establishment devices 106 (as explained in more detail in relation to the toilet event component 124). The patient event component 128 may increase a time period until a next predicted toilet need event based on the toileting event taking place.

In an illustrative example, the first toilet need schedule may be characterized by a predicted toilet need every two hours, based on conditions in the EMR 118 of the patient, and may supply notifications to the clinician device 104 according to the predicted toilet need. The patient event component 128 may receive an indication of a toileting event from the patient relief device 102, such as prior to a predicted toilet need according to the first toilet need schedule. Upon receiving the indication of the toileting event, the patient event component 128 may increase the two hour time period until a next predicted toilet need to three hours, and may cause the second toilet need schedule to be characterized by the updated predicted toilet need. The patient event component 128 may provide a notification to the clinician device 104 associated with the healthcare provider so that the healthcare provider is present for the toileting need of the second toilet need schedule. In at least some examples, the indication of the event may include a measurement of a void associated with the event as well, and the updated predicted toilet need may be based on a value representing the measurement. For instance, the time period until the updated predicted toilet need may be greater if there is a larger void measurement value.

The patient event component 128 may, in some cases, utilize the machine-learned models 120 to predict times at which the patient will experience a toileting need, and may use the predicted times to determine the second toilet need schedule. For example, the patient event component 128 may input the event associated with the patient into the machine-learned model 120, and receive, from the machine-learned model 120, a prediction of a time at which the patient will experience a toileting need. In some examples, the patient event component 128 may input the condition(s) of the patient and/or the first toilet need schedule into the machine-learned model in addition to the event, which may increase the accuracy of the prediction of the time at which the patient will experience the toileting need. The patient event component 128 may use a subject fixed-effect model and/or a subject random-effect model, similar to the discussion above, to predict the time at which the patient will experience the toileting need to be included in the second toilet need schedule. In many examples, the patient event component 128 may continue to input events and/or conditions associated with the patient into the machine-learned model 120, which may in turn increase accuracy of the predictions of times at which the patient will experience a toileting need by the machine-learned model 120 as the machine-learned model 120 "learns" the toileting preferences and needs of the patient.

In some cases, an event may cause the patient event component 128 to override the first toilet need schedule for at least a period of time. For example, some medications, such as Lasix®, may cause a patient to urinate at a particular frequency following administration of the medication. If the patient event component 128 receives an indication of an event that includes administration of a medication to the patient that affects a frequency of urine output or bowel movements, the patient event component 128 may generate the second toilet need schedule accordingly.

For instance, the patient event component 128 may determine a rule that corresponds to toileting times associated with the medication, where the rule may be stored in association with the medication in the database 116. The patient event component 128 may determine that the rule overrides the predicted toilet need times included in the first toilet need schedule (or a subsequent toilet need schedule, such as the second toilet need schedule). In at least some examples, the patient event component 128 may receive the first toilet need schedule from the condition component, where the first toilet need schedule is based at least in part on a predicted time at which the patient will experience a toileting need received from the machine-learned model 120. In some cases, the patient event component 128 may override the predicted time at which the patient will experience the toileting need received from the machine-learned model 120 based on the rule associated with the medication as indicated by the event. In other words, the toilet scheduling component 122 may employ a combination of the machine-learned models 120 and algorithms relying on rules stored in the database 116 to more accurately anticipate patient needs associated with toileting.

In some examples, the dispatch component 130 may be configured to provide a notification associated with the second toilet need schedule to the patient relief device 102, the clinician device 104, and/or the healthcare establishment device 106, where the notification indicates a prediction of a toilet need of the patient. The dispatch component 130 may provide the notification at a time prior to the predicted toilet need of the patient, such that a healthcare provider has enough time to conclude a current task and/or travel to the location of the patient to assist with the toileting need. For example, the dispatch component 130 may determine a location of the healthcare provider based on a real-time location service (RLTS) included in the clinician device 104 associated with the healthcare provider, determine a travel time from the location of the healthcare provider to the location of the patient, and provide the notification to the clinician device 104 at a time that allows the healthcare provider to travel the distance to the patient. The dispatch component 130 may also provide the notification to allow extra time for patients with inhibited mobility to reach the toilet, and/or provide the notification based on a preference of the patient (e.g., urgency and/or frequency of toileting needs of the patient as described above). Additionally, the dispatch component 130 may provide notifications to multiple ones of the clinician devices 104, such as in cases where multiple healthcare providers may be required to transport the patient from a hospital bed to the patient relief device 102. Furthermore, the dispatch component 130 may use a patient's weight to determine a particular healthcare provider that is capable of assisting the patient, and/or multiple providers that may be needed to assist the patient with accessing the patient relief device 102, and provide notifications to associated clinician device(s) accordingly.

In some cases, the dispatch component 130 may provide the notification to the clinician device 104 associated with a particular healthcare provider based on the location of the healthcare provider and an urgency of the patient relative to other patients who may also be experiencing a toileting need. For instance, the dispatch component 130 may determine a first minimum amount of time required to conduct a toileting event after a notice is received (e.g., a call is placed) from a first patient. Similarly, the dispatch component 130 may determine a second minimum amount of time required to conduct a toileting event after a notice is received from a second patient, a third minimum amount of time required to conduct a toileting event after a notice is received from a third patient, and so on. The dispatch component 130 may determine the minimum amounts of time based on preferences of the respective patients, such as an urgency determined over time for the respective patients using the machine-learned model 120 and/or provided by the patients themselves or a healthcare provider and accessed from the database 116. Alternatively or additionally, the dispatch component 130 may determine the minimum amounts of time based on a mobility of the respective patients, a number of healthcare providers needed to assist the respective patients, one or more devices required (e.g., a walker, an overhead lift, etc.) to assist the respective patients to the patient relief device 102, and so forth. In many examples, different patients will have different minimum amounts of time required to conduct toileting events based on the factors described herein.

The dispatch component 130 may prioritize a dispatch of one or more healthcare providers to assist with the toileting events of the various patients from which notice was received based on the respective minimum amounts of time associated with the different patients. In some examples, the dispatch component 130 may dispatch a healthcare provider to patients that have a shorter minimum amounts of time than patients that have longer minimum amounts of time. In an illustrative example, the dispatch component 130 may provide a notification to a clinician device 104 instructing a healthcare provider to dispatch to a first patient having a minimum amount of time required to conduct a toileting event of two minutes, and withhold a notification instructing the healthcare provider to dispatch to a second patient having a minimum amount of time required to conduct a toileting event of fifteen minutes until after the toileting event of the first patient is complete. In some cases, the notification may indicate a priority of the multiple patients from which notice was received, such as in a listed format determined based on the minimum times associated with the respective patients.

In some examples, a patient may not be thinking about toileting needs until after a healthcare provider checks on the patient and inquires about a toileting need. Often, when a healthcare provider inquires about the toileting need, the patient will realize there is a toileting need a moment after the healthcare provider leaves the room of the patient, then attempt to call the healthcare provider back to the room to provide assistance with the toileting need. In such cases, the dispatch component 130 may determine which healthcare provider to assist with the toileting need based on locations of different healthcare providers relative to the room of the patient.

For instance, the dispatch component 130 may receive a call notification from a patient. In response to receiving the call notification, the dispatch component 130 may determine an amount of time between a visit to the room of the patient by a healthcare provider and the call notification. If the amount of time is less than a threshold amount of time (e.g., less than one minute, less than 3 minutes, less than 5 minutes, etc.), the dispatch component 130 may determine that the call notification may be associated with a toileting need of the patient. Alternatively or additionally, the dispatch component 130 may determine whether there was a toileting event while the healthcare provider was visiting the room of the patient, such as based on information received from the patient relief device 102, the clinician device 104, and/or the healthcare establishment devices 106. If there was no toileting event during the visit by the healthcare provider to the room of the patient, the dispatch component 130 may determine that the call notification may be associated with a toileting need of the patient.

Additionally, the dispatch component 130 may determine a location of the healthcare provider that visited the room of the patient, and/or one or more other healthcare providers, such as based on RLTS information provided by the clinician devices 104 associated with the respective healthcare providers. In at least some examples, the dispatch component 130 may direct the call notification to a healthcare provider that is nearest the room of the patient, independent of whether the nearest healthcare provider was the healthcare provider that visited the room of the patient. The dispatch component 130 may take tasks being performed by the healthcare provider into account as well. For example, if the nearest healthcare provider is resuscitating a different patient, the dispatch component 130 may select a different healthcare provider to direct the call notification to related to the toileting need of the patient.

Further, the dispatch component 130 may direct notifications to different types of healthcare providers based on the type of toileting need of the patient and what types of treatments the different types of healthcare providers are qualified to perform. In an illustrative example, if a patient needs assistance with walking to the patient relief device 102 to attempt a void, but does not require specialized care, the dispatch component 130 may direct the notification related to the toileting need of the patient to a medical technician. In another illustrative example, if the patient requires a catheter to be placed, the dispatch component 130 may direct the notification related to the toileting need of the patient to a physician who specializes in catheter placement.

To appropriately dispatch notifications to different types of healthcare providers, the dispatch component 130 may determine a treatment to administer to the patient based on the toilet need schedule. Treatments may include mobility assistance (assisting the patient to exit a bed or chair, assisting the patient with ambulating to the patient relief device 102, etc.), administration of medication associated with toileting, changing of an incontinence product or bedding, catheter placement or removal, and so forth. The dispatch component 130 may also determine types of treatments provided by different types of healthcare providers, which may be stored in the database 116. The dispatch component 130 may select a type of healthcare provider based on the treatments provided by the healthcare provider type and the toileting need of the patient. In some examples, the dispatch component 130 provides the notification to a clinician device 104 associated with a healthcare provider of the healthcare provider type that provides the type of treatment associated with the toileting need of the patient. Further, the dispatch component 130 may indicate the type of treatment required by the patient in the notification provided to the clinician device 104 associated with the healthcare provider.

Figure 2:
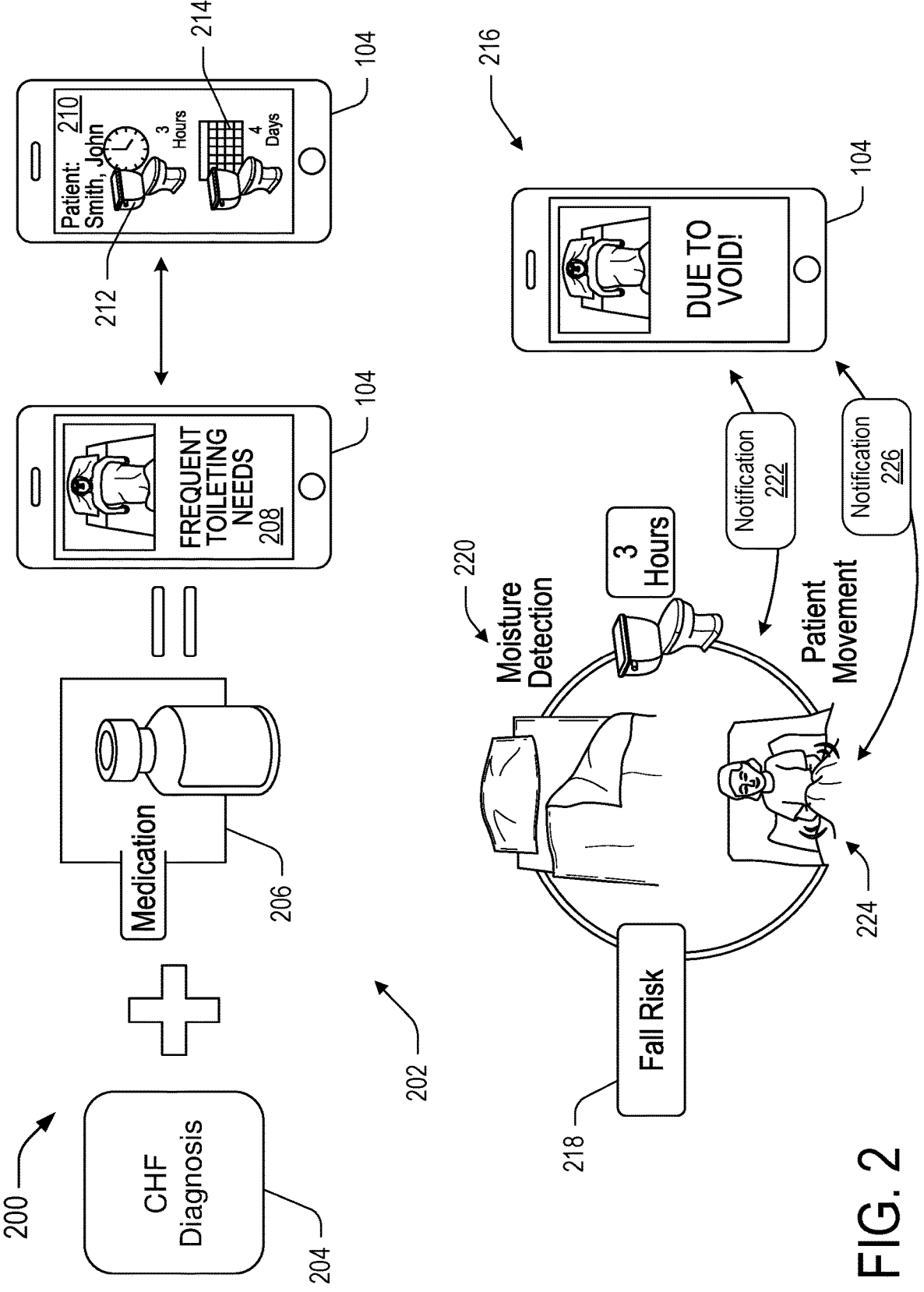
FIG. 2 is a schematic illustration of how toilet need schedules may be generated, updated, and provided to a healthcare provider, in accordance with examples of the disclosure.

FIG. 2 is an example system 200 indicating how toilet need schedules may be generated, updated, and provided to a healthcare provider, in accordance with examples of the disclosure. For example, the example system 200 includes a first schematic illustration 202 indicating how the toilet scheduling component 122 of FIG. 1 may generate a toilet need schedule for a patient based on a condition 204 of the patient and an event 206 associated with the patient. As described above, the condition component 126 of FIG. 1 may receive the condition 204 of the patient from the EMR 118 associated with the patient. In the illustrated example, the condition 204 indicates that the patient has a congestive heart failure (CHF) diagnosis. In other examples, it is understood that the patient may have a CHF diagnosis or other diagnoses impacting the toileting needs of the patient. For instance, in many cases, CHF symptoms may affect toileting needs of the patient, such as by causing sudden urges to urinate. Therefore, the condition component 126 may determine a first toilet need schedule for the patient based on the symptoms associated with CHF, such as by increasing a frequency at which a healthcare provider checks in on the patient to see if the patient feels the need to urinate.

Additionally, in some examples, the dispatch component 130 may utilize information related to the condition 204 as well. For instance, the condition component 126 may store a minimum amount of time required to conduct a toileting event after notice is received from the patient in the EMR 118 based on the condition 204. The dispatch component 130 may prioritize dispatch of healthcare providers based on the minimum amount of time required, as described above. Because CHF may increase an urgency associated with toileting events, the minimum amount of time required to conduct a toileting event after notice is received from the patient may be less than other patients that do not have CHF, and thus the dispatch component 130 may prioritize dispatch of healthcare providers to assist the patient over other patients that do not have CHF. Other conditions that may trigger an increased urination need are urinary tract infection, diabetes type 1 or 2, prostatitis, kidney infection, diabetes insipidus, urinary bladder stones, benign prostatic hyperplasia, interstitial cystitis, urethral stricture, and Urinary Incontinence.

Additionally, the event component 128 of FIG. 1 may receive an indication of the event 206, in this case administration of a medication, such as Lasix® (or other diuretic), to the patient. Lasix® is a medication commonly used to treat edema (extra fluid in the body) caused by conditions such as heart failure, which may also be associated with CHF. In the process of eliminating the extra fluid from the patient's body, Lasix® may increase a frequency at which the patient needs to urinate, which may be as frequent as every 20 minutes. Accordingly, in response to receiving the indication of the event 206, the event component 128 may determine the second toilet need schedule for the patient to increase the frequency to check on the toileting needs of the patient to every 20 minutes for a time period associated with the effect of Lasix®, such as for two hours. Following the conclusion of the time period associated with the effect of Lasix®, the toilet scheduling component 122 may resume the first toilet need schedule, or may determine a third toilet need schedule that is different than the first toilet need schedule and the second toilet need schedule based on other events associated with the patient.

The schematic illustration 202 also depicts an example of a user interface 208 and a user interface 210, which may be displayed by the clinician device 104 of FIG. 1. The clinician device 104 may display the user interface 208 in response to receiving a notification from the patient event component 128 associated with a toilet need schedule for the patient. As shown, the user interface 208 indicates that the patient will have frequent toileting needs. The indication in the user interface 208 may be based on the condition 204 and/or the event 206.

Additionally, the clinician device 104 may display the user interface 210 in response to receiving a notification from the patient event component 128 associated with a toilet need schedule for the patient. The user interface 210 includes additional details associated with the patient than are included in the user interface 208. For example, the user interface 210 includes an icon 212 indicating a time period associated with predicted toileting needs according to the toilet need schedule of the patient, in this case that the patient is predicted to have a toileting need every 3 hours. Further, the user interface 210 includes an icon 214 indicating a time period (e.g., a duration) of the toilet need schedule associated with the patient, in this case that the toilet need schedule is 4 days in duration.

The example system 200 also includes a schematic illustration 216, indicating how the toilet scheduling component 122 of FIG. 1 may generate and continuously update a toilet need schedule for a patient based on a condition 218 of the patient and events associated with the patient. As described above, the condition component 126 of FIG. 1 may receive the condition 218 of the patient from the EMR 118 associated with the patient. In the illustrated example, the condition 218 indicates that the patient has a fall risk. Because the patient has a fall risk, the patient may need additional time to traverse from a hospital bed or chair to the patient relief device 102 of FIG. 1, and/or may need additional assistance (e.g., additional personnel, use of a mobility device such as an overhead lift or walker, etc.) to traverse from a hospital bed or chair to the patient relief device 102. Therefore, the condition component 126 may incorporate the additional time and/or assistance required by the fall risk into the toilet need schedule for the patient, such as by providing notifications to multiple healthcare providers, sending notifications earlier to provide more time to assist the patient to the patient relief device, and so forth.

The schematic illustration 216 further includes an indication of an event 220, which in this case corresponds to a healthcare establishment device 106 such as a hospital bed detecting moisture (e.g., urination by the patient in the hospital bed). The healthcare establishment device 106 provides an indication of the event 220 to the event component 128 of FIG. 1. The event component 128 may determine that the event 220 is associated with a toileting event by the patient. In some examples, the event component 128 may determine a second toilet need schedule based on the event 220, such as by resetting a time at which to check on the patient for a subsequent toileting need. In the illustrated example, the second toilet need schedule may include a predicted time at which the patient will experience a toileting need based on the event 220, in this case 3 hours after the event 220.

In at least some examples, the dispatch component 130 provides a notification 222 to the clinician device 104 at a time based on the second toilet need schedule (e.g., subsequent to the event 220), as well as based on the condition 218. For example, the event component 128 may determine that the next predicted toileting need of the patient is 3 hours after the event 220. Based on the condition 218, the dispatch component 130 may provide the notification 222 prior to the next predicted toileting need, to account for additional time and/or assistance required for the condition 218. In an illustrative example, the dispatch component 130 may provide the notification 222 to the clinician device 104 at 20 minutes prior to the time associated with the predicted toileting need.

In some cases, a healthcare provider may check on the patient according to the schedule, such as after receiving the notification 222, to determine if the patient has a toileting need. The patient may indicate that they do not currently have a toileting need at the time of the check-in, so the healthcare provider may leave the room of the patient. As shown, the schematic illustration 216 also includes an indication of an event 224, which in this case corresponds to the healthcare establishment device 106 detecting movement by the patient. In some instances, movement by the patient may indicate that the patient has a toileting need. The healthcare establishment device 106 provides an indication of the event 224 to the event component 128 of FIG. 1. The event component 128 may determine that the event 224 is associated with a toileting need of the patient. In some examples, the dispatch component 130 may provide a notification 226 to the clinician device 104. As described above, the dispatch component 130 may provide the notification 226 based on a proximity of the healthcare provider associated with the clinician device 104 to the hospital room of the patient. Accordingly, the notification 226 may be provided to a different clinician device 104 associated with a different healthcare provider than visited the room of the patient in response to the notification 222.

In some examples, the event component 128 may update the second toilet need schedule based on the event 224, such as by resetting a time at which to check on the patient for a subsequent toileting need. For example, the event component 128 may determine that the patient had a toileting event following the notification 226, such as based on information provided by the patient relief device 102, the clinician device 104, and/or the healthcare establishment device 106. In response to the indication of the toileting of the event by the patient, the event component 128 may reset the predicted time (e.g., 3 hours) following the toileting event at which to check on the next toileting need of the patient.

Figure 3:
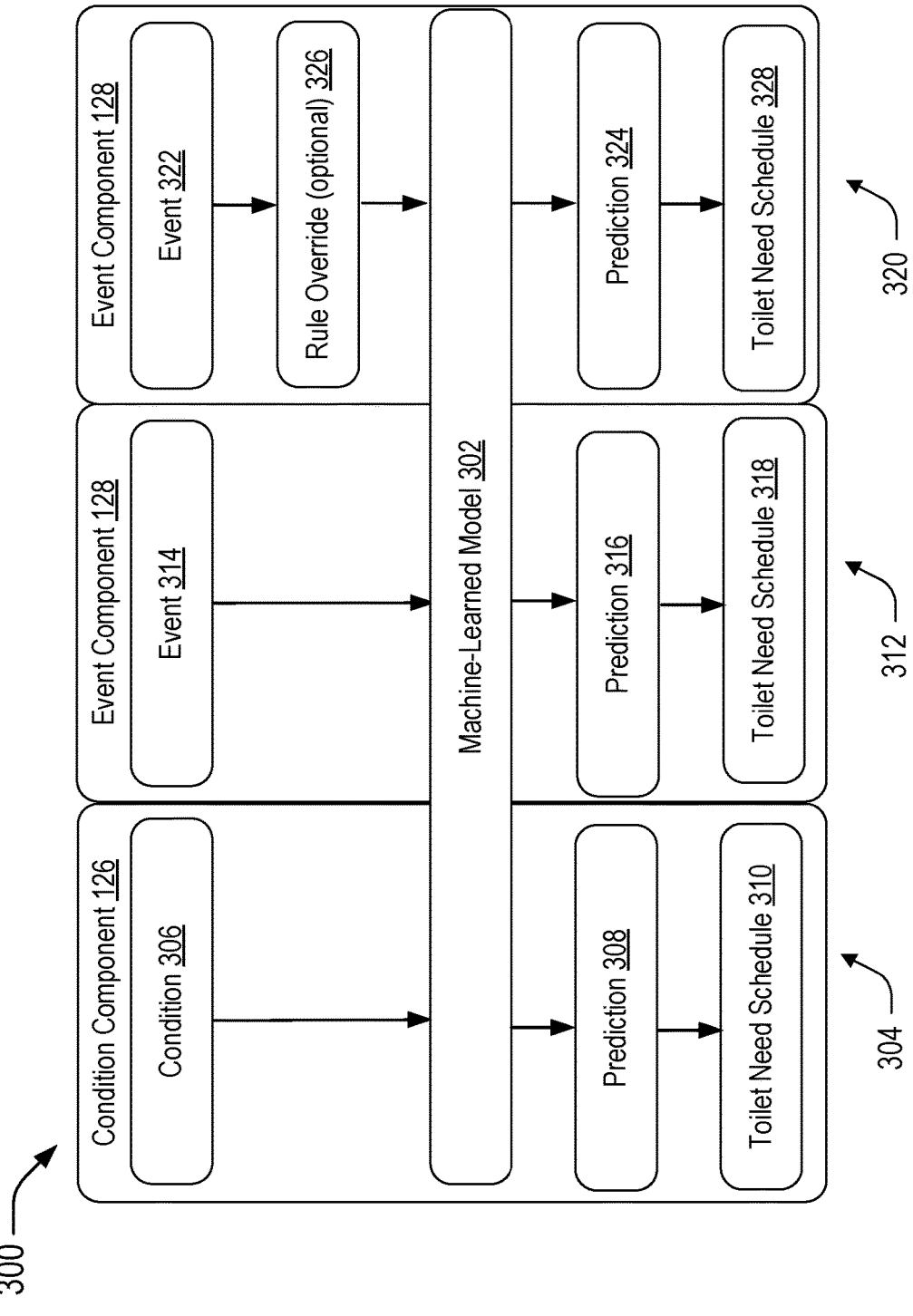
FIG. 3 is a schematic illustration of utilizing a machine-learned model to generate and update a toilet need schedule, in accordance with examples of the disclosure.

FIG. 3 is a schematic illustration depicting an example system 300 which utilizes a machine-learned model 302 to generate and update a toilet need schedule, in accordance with examples of the disclosure. For example, at a time 304, the machine-learned model 302 may receive a condition 306 associated with a patient. The condition 306 may be indicated in the EMR 118 of the patient, and determined from the EMR 118 by the condition component 126 of FIG. 1. As described above, the machine-learned model 302 may be a subject fixed-effect model and/or a subject random-effect model trained to determine predictions of times at which a patient will experience a toileting need based on one or more conditions associated with the patient and/or one or more events associated with the patient. Accordingly, the machine-learned model 302 may output a prediction 308 of a time at which the patient will experience a toileting need based on the condition 306. The condition component 126 may determine a toilet need schedule 310 based at least in part on the prediction 308. For example, the condition component 126 may determine an amount of time prior to the prediction 308 that a healthcare provider should check on the patient based on the patient's need for assistance to reach a patient relief device.

At a time 312, the machine-learned model 302 may receive an indication of an event 314 associated with the patient. In at least some examples, the event 314 may be related to a toileting need of the patient, such as an event that increases or decreases an amount of time between toileting events of the patient, or may be a toileting event itself. The machine-learned model 302 may output a prediction 316 of a time at which the patient will experience a toileting need based at least in part on the event 314 and the condition 306.

In at least some examples, the machine-learned model 302 begins to "learn" about the toileting needs of the patient as events associated with toileting, such as the event 314, begin to occur. For instance, the machine-learned model 302 may "learn" how frequently the patient experiences toileting needs, an urgency associated with the patient's toileting needs, how meals affect the patient's toileting needs, how beverages affect the patient's toileting needs, how medications affect the patient's toileting needs, and so forth. In this way, the machine-learned model 302 improves subsequent predictions of toileting needs of the patient based on the condition 306 and events over time. Improved predictions may increase safety and reduce accidents for the patient by dispatching healthcare providers in anticipation of toileting needs of the patient, rather than the healthcare providers reacting to toileting needs after a toileting event occurs or on a schedule that is not customized to the patient.

The event component 128 may determine a toilet need schedule 318 based at least in part on the prediction 316. In some cases, the toilet need schedule 318 may be a modification of the toilet need schedule 310 based on the occurrence of the event 314. In an illustrative example, the toilet need schedule 310 may include a 2-hour increment at which to check on the toileting need of the patient. The event 314 may be associated with a toileting event one hour into the 2-hour increment. Accordingly, the machine-learned model 302 may determine the prediction 316 to be one hour rather than 2 hours to check on a subsequent toileting need for the patient. It should be considered that any number of events, similar to the event 314, may take place that may affect a toilet need schedule associated with the patient.

At a time 320, the machine-learned model 302 may receive an indication of an event 322 associated with the patient, subsequent to the event 314. Similar to the event 314, the event 320 may be related to a toileting need of the patient, such as an event that increases or decreases an amount of time between toileting events of the patient, or may be a toileting event itself. The machine-learned model 302 may output a prediction 324 of a time at which the patient will experience a toileting need based at least in part on the event 322, the event 314, and the condition 306.

In some examples, event component 128 may determine that the event 322 is associated with a rule override 326. For instance, the rule override 326 may be based on a medication administered to the patient that causes the patient to experience a toileting need at a predetermined time (e.g., 20 minutes) following administration of the medication. Therefore, the event component 128 may override the prediction 324 provided by the machine-learned model 302 to determine a toilet need schedule 328 based on the event 322. Alternatively, instead of completing overriding the prediction 324, the rule override 326 may affect the prediction of a toileting need. For example, the rule override 326 may affect the machine-learned model 302 prediction and alter such prediction to predict a toileting need for the patient in twenty minutes instead of thirty. In this way, the event component 128 can ensure that a healthcare provider checks on the toileting need of the patient at a schedule determined by the medication indicated in the event 322. In some cases, the machine-learned model 302 may "learn" the schedule associated with the medication indicated in the event 322, and how the patient reacts to the medication indicated in the event 322. In an illustrative example, if the rule override 326 indicates that the healthcare provider should check on the patient 20 minutes after administration of the medication, but the patient experiences the toileting need 15 minutes after administration of the medication, the machine-learned model 302 may make subsequent predictions based on the specific need of the patient when the medication is administered.

FIG. 4 is an example process 400 for determining and updating a toilet need schedule, according to the techniques described herein. In some examples, one or more operations of the process 400 may be combined with one or more operations of the method illustrated in FIG. 6. In some examples, the process 400 may be performed by one or more processors of computing devices, such as the patient management system 108 of FIG. 1.

At operation 402, the toilet scheduling component 122 receives information indicating a condition associated with a patient. For example, the condition component 126 of the toilet scheduling component 122 may receive an EMR 118 associated with the patient, and determine one or more conditions associated with the patient from the EMR 118. In some cases, the condition may affect toileting needs of the patient. Some examples of conditions that the condition component 126 may determine from the EMR 118 may include a medication administered to the patient that affects a frequency of urine output or bowel movements, an intravenous (IV) fluid dosage administered to the patient, a disease of the patient, a pregnancy of the patient, a demographic of the patient, an age of the patient, a body mass index (BMI) of the patient, a presence of a catheter on the patient, a presence of an incontinence management device (e.g., a diaper) on the patient, a colostomy or an ostomy on the patient, mobility of the patient, and so forth. Medications that may affect frequency of urine output or bowel movements may include, for instance, Lasix®, diuretics, stool softeners, and the like. Diseases of the patient that may affect frequency of urine output or bowel movements may include, for example, urinary tract infections (UTIs), chronic obstructive pulmonary disease (COPD), edema, nephrology, benign prostatic hyperplasia, diabetes, a clostridium difficile (C-diff) infection, anuria, and so on.

At operation 403, the toilet scheduling component 122 may determine if a rule override has occurred. If a rule override has occurred, then the specific rule override may completely overrule any toileting need schedule that would have been predicted by the toilet scheduling component 122. Thus, as shown in example process 400, the process would proceed to operation 412 and send a prediction of a toilet need completely based on the rule override. Example medications that may trigger a rule override are an intravenous fluid bolus with a normal saline (0.9% sodium chloride), lactated ringers (LR), diuretics with a 40 mg IV ×1 dose, or diuretics with a Torsemide 20 mg orally×1 dose. As described above, while not shown in example process 400, there may be scenarios where the rule override only modifies and does not completely overrule the toilet need prediction generated by the toilet scheduling component 122, for example, accelerating the toilet need schedule by a percentage associated with the override rule. If a rule override has not occurred, the example process 400 may proceed to operation 404.

At operation 404, the toilet scheduling component 122 determines a first toilet need schedule for the patient based at least in part on the condition, where the first toilet need schedule corresponds to a time period. In some examples, the time period may be a fixed time period or a variable time period. For instance, a fixed time period corresponding to the first toilet need schedule may be associated with an 8-hour or a 12-hour shift for a healthcare provider (e.g., a nurse) who is assigned to care for the patient, and the first toilet need schedule may predict a number of toileting events to occur during the fixed time periods and times at which such predicted toileting events will occur. A variable time period corresponding to the first toilet need schedule may be associated with a time at which a next toileting event is predicted to occur based on the condition(s) of the patient, such as by providing a countdown to a predicted next toileting event.

To determine the first toilet need schedule, the condition component 126 of the toilet scheduling component 122, may employ one or more rules-based algorithms, and/or the machine-learned models 120. For instance, the condition component 126 may input the condition associated with the patient into the machine-learned model 120, and receive a prediction of a time at which the patient will experience a toileting need from the machine-learned model 120. The condition component 126 may use the prediction of the time at which the patient will experience the toileting need to determine the first toilet need schedule. Additionally, in some cases, the condition component 126 may provide time in the first toilet need schedule based on an amount of time that the patient will need, and/or an amount of assistance the patient will need to reach a patient relief device for a toileting event when determining the first toilet need schedule.

At operation 406, the toilet scheduling component 122 receives, from a first device, an indication of an event associated with the patient. The patient event component 128 of the toilet scheduling component 122 may receive the indication of the event from the patient relief device 102, the clinician device 104, and/or the healthcare establishment device 106. As described above, an "event" refers to an event that may have an effect on a toileting need of a patient, such as a meal eaten by the patient, a feeding administered to the patient via a feeding tube, a beverage consumed by the patient, a medication administered to the patient, an instance of a toileting event by the patient, a preference of the patient associated with toileting events, and so forth.

At operation 408, the toilet scheduling component 122 determines whether the event affects the first toilet need schedule. For instance, the event component 128 may receive an indication of an event such as a medication administered to the patient, but the event component 128 may determine that the particular medication that was administered does not affect toileting needs of the patient. If the toilet scheduling component 122 determines that the event does not affect the first toilet need schedule (e.g., "No" at operation 408), the process 400 returns to the operation 406, until the toilet scheduling component 122 receives an indication of another event from the first device (or a different device).

If the toilet scheduling component 122 determines that the event does affect the first toilet need schedule (e.g., "Yes" at operation 408), the process 400 proceeds to operation 410. The operation 410 includes the toilet scheduling component 122 determining a second toilet need schedule for the patient based at least in part on the condition and the event. The second toilet need schedule of the operation 410 corresponds to the time period and is different than the first toilet need schedule. For instance, the first toilet need schedule may correspond to a fixed time period such as a shift of one or more healthcare providers, as described herein. The first toilet need schedule, based at least in part on the condition of the patient, may include a time at which a predicted toilet need will occur. When an event such as administration of a medication or consuming a meal occurs, the event may impact the time at which the predicted toilet need will occur. Accordingly, the patient event component 128 updates a toilet need schedule of a patient based on events that occur related to the patient so that the healthcare providers can provide care that is needed and avoid unnecessary visits when toileting events are unlikely.

The patient event component 128 may, in some cases, utilize the machine-learned models 120 to predict times at which the patient will experience a toileting need, and may use the predicted times to determine the second toilet need schedule. For example, the patient event component 128 may input the event associated with the patient into the machine-learned model 120, and receive, from the machine-learned model 120, a prediction of a time at which the patient will experience a toileting need. In some examples, the patient event component 128 may input the condition(s) of the patient and/or the first toilet need schedule into the machine-learned model in addition to the event, which may increase the accuracy of the prediction of the time at which the patient will experience the toileting need. The patient event component 128 may use a subject fixed-effect model and/or a subject random-effect model, similar to the discussion above, to predict the time at which the patient will experience the toileting need to be included in the second toilet need schedule. In many examples, the patient event component 128 may continue to input events and/or conditions associated with the patient into the machine-learned model 120, which may in turn increase accuracy of the predictions of times at which the patient will experience a toileting need by the machine-learned model 120 as the machine-learned model 120 "learns" the toileting preferences and needs of the patient.

At operation 412, the toilet scheduling component 122 provides, to a second device, a notification associated with the second toilet need schedule, where the notification indicates a prediction of a toilet need of the patient. For instance, the dispatch component 130 of the toilet scheduling component 122 provides a notification associated with the first toilet need schedule and/or the second toilet need schedule to one or more of the clinician devices 104 via the network 110. As mentioned above, the first toilet need schedule and/or the second toilet need schedule may comprise a fixed time period, such as a shift duration of a healthcare provider. In such cases, the dispatch component 130 may provide the first toilet need schedule and/or the second toilet need schedule associated with the fixed time period, including predicted times at which the patient will have a toileting need, to the clinician device 104. In this way, a healthcare provider that receives a toilet need schedule associated with the fixed time period at the clinician device 104 may view upcoming predicted toileting needs of the patient, and execute tasks accordingly.

Alternatively or additionally as described above, the first toilet need schedule and/or the second toilet need schedule may comprise a variable time period, such as a countdown to a next predicted toileting need of the patient. In such cases, the dispatch component 130 may determine a clinician device 104 associated with a particular healthcare provider to provide the notification associated with the first toilet need schedule to, such as based on a location of the clinician device 104 (e.g., in cases where the clinician device 104 is a mobile device carried by a healthcare provider) relative to the patient, a task being performed by the healthcare provider associated with the clinician device 104, and the like. Therefore, the dispatch component 130 may dynamically direct healthcare providers to patients predicted to have upcoming toileting needs based on location and/or availability of the healthcare providers. Additionally, the dispatch component 130 may utilize the machine-learned models 120 to determine toilet need schedules and/or provide notifications related to dispatching healthcare providers to one or more patients to assist with toileting events, as described above.

Toilet Event Sensing

Returning to the discussion of FIG. 1, the patient management system 108 may include a toilet event component 124 configured to detect a patient moving towards (or attempting to move towards) the patient relief device 102, detect that the patient is using the patient relief device 102, and/or detect that the patient has concluded using the patient relief device 102, along with providing notifications to healthcare providers to assist with toileting needs of the patient as appropriate. By detecting events associated with toileting as described herein, the toilet event component 124 provides information to healthcare providers relating to the toilet events in real time, while maintaining patient privacy related to the toileting events. Therefore, risks associated with toileting events may be reduced without intrusive conditions imposed upon patients.

In some examples, the toilet event component 122 includes a sensor analysis component 132 configured to receive sensor data associated with toileting events and determine a progression of the toileting event from the sensor data. For example, the sensor analysis component 122 may receive sensor data from the one or more sensors 112 associated with the patient relief device 102, such as a pressure sensor associated with a seat of the patient relief device 102, a heartrate sensor associated with a seat of the patient relief device 102, a respiration sensor associated with a seat of the patient relief device 102, a motion sensor associated with the patient relief device 102, a flush sensor associated with the patient relief device 102, a liquid volume sensor associated with the patient relief device 102, and so forth. Alternatively or additionally, the sensor analysis component 122 may receive sensor data from one or more sensors from the healthcare establishment device(s) 106, such as a pressure sensor (e.g., included in a hospital bed, a chair, the floor, etc.), a light beam sensor that senses interruptions of a light beam when objects pass through the light beam, a real time location sensor (RTLS) (e.g., included in a gown, a sock, a bracelet, an incontinence device, etc.) worn by the patient, a motion sensor, a radar sensor, a camera, a microphone, and so on. In some cases, the sensor analysis component 122 may receive data from the clinician device 104, such as inputs by a healthcare provider related to toileting events, data from a RTLS sensor, data from a motion sensor, and the like.

In at least some examples, the sensor analysis component 132 may determine, based at least in part on the sensor data, that a patient is moving or attempting to move towards the patient relief device 102. Because many patients require assistance to move to the patient relief device 102 from a hospital bed or a chair, for instance, providing notification of such an event to a healthcare provider may prevent injuries and/or accidents from occurring. Therefore, upon the sensor analysis component 132 detecting the patient moving or attempting to move towards the patient relief device 102, a notification component 134 may provide a notification to the clinician device 104 and/or a healthcare establishment device 106 of the patient moving or attempting to move towards the patient relief device 102. For example, the notification component 134 may send a notification to the clinician device 104 that includes a message such as "Patient Assistance Needed for Toileting", and/or may change a color of a light outside of the patient's room from one color to a different color, indicating that assistance is needed inside of the room.

Following are several non-limiting, illustrative examples of determining that the patient is moving or attempting to move towards the patient relief device 102, and notifications indicating such. In some cases, the sensor analysis component 132 may receive sensor data from multiple sensors (e.g., according to the illustrative examples below or otherwise) and determine that the patient is moving or attempting to move towards the patient relief device 102 based on the sensor data received from the different sensors.

For instance, the sensor analysis component 132 may receive sensor data from a pressure sensor associated with a hospital bed or a chair. The sensor analysis component 132 may determine, based on the sensor data received from the pressure sensor, movement by the patient relative to the pressure sensor, and that the movement may correspond to the patient moving or attempting to move to the patient relief device 102. Accordingly, the notification component 134 may provide a notification to the clinician device 104 to check on the patient to see if the patient is moving or attempting to move to the patient relief device 102, or if the patient has another need to be attended to by the healthcare provider.

In another example, the sensor analysis component 132 may receive sensor data from a light beam sensor. For instance, a light beam sensor may be configured to detect the presence or absence of a light beam (such as a laser, infrared beam, or the like) originating from a light source. When the light beam is interrupted by an object (such as the patient), the absence of the light beam may indicate that the object is occupying space between the light source and the light beam sensor. Accordingly, the light source and the light beam sensor may be located in positions such that when the light beam is interrupted, it may be indicative of the patient moving towards or attempting to move towards the patient relief device. Example positions of the light source and/or the light beam sensor may include a doorway or entryway to a bathroom, a position proximate the patient relief device 102 where the patient may stand or sit in preparation to use the patient relief device 102, and so forth. In response to the sensor analysis component 132 determining from the sensor data from the light beam sensor that the patient is moving towards or attempting to move towards the patient relief device 102, the notification component 134 may provide a notification to the clinician device 104 to check on the patient to see if the patient is moving or attempting to move to the patient relief device 102, or if the patient has another need to be attended to by the healthcare provider.

In another example, the sensor analysis component 132 may receive sensor data (e.g., audio data) from a microphone located in a hospital room of the patient, which may also include a bathroom. In some cases, a change in volume of the audio data detected by the microphone may indicate a change in a location of the patient, such as the patient getting closer or farther away from the patient relief device 102. The sensor analysis component 132 may determine, based on the audio data received from the microphone, movement and/or a change in location of the patient, and that the movement or change in location may correspond to the patient moving or attempting to move to the patient relief device 102. Accordingly, the notification component 134 may provide a notification to the clinician device 104 to check on the patient to see if the patient is moving or attempting to move to the patient relief device 102, or if the patient has another need to be attended to by the healthcare provider.

In yet another example, the sensor analysis component 132 may receive sensor data from one or more sensors that indicates a change in a location of the patient. Sensors that may indicate a change in a location of the patient may include, for instance, RTLS sensors, motion sensors, radar sensors, lidar sensors, cameras, and so forth. The sensor analysis component 132 may determine, based on the change in the location of the patient indicated by the sensor data, that the patient is moving or attempting to move to the patient relief device 102. For example, the sensor analysis component 132 may determine, based on the sensor data, that the patient is moving toward a side of a hospital bed, and/or that the patient is moving toward a bathroom adjacent the patient's hospital room. Based on the sensor analysis component 132 determining the change in the location of the patient, the notification component 134 may provide a notification to the clinician device 104 to check on the patient to see if the patient is moving or attempting to move to the patient relief device 102, or if the patient has another need to be attended to by the healthcare provider.

In examples in which the healthcare establishment device 106 includes a camera configured to capture images or video and determine, from the images or video, a change in a location of the patient, the sensor analysis component 132 may be configured to identify whether the person moving or attempting to move toward the patient relief device is the patient or a different person. Often, other people are in a patient's room than the patient themselves, such as healthcare providers or visitors for the patient. When people other than the patient move towards the patient relief device, the sensor analysis component 132 may detect, from an image or video, that someone other than the patient is moving towards the patient relief device and cause the notification component 134 to withhold a notification to the clinician device 104.

For instance, the sensor analysis component 132 may select the patient from multiple people depicted in an image or a video, such as using facial recognition of the patient (and/or of other people in the image or video). The sensor analysis component 132 may determine whether the patient is moving in the images or video, or if another person depicted in the images or video is moving. If the sensor analysis component 132 determines that the patient is moving, and that the patient is moving towards the patient relief device 102, the notification component 134 may send a notification to the clinician device 104 to request assistance for the patient to reach the patient relief device 102. Alternatively or additionally, if the sensor analysis component 132 determines that a person other than the patient is moving, the notification component 134 may withhold a notification to the clinician device 104 for assistance to reach the patient relief device 102. For instance, the sensor analysis component 132 may determine that the person other than the patient who is moving toward the patient relief device 102 is a healthcare provider and is assisting the patient to reach the patient relief device 102, and may withhold calling an additional healthcare provider who may not be needed.

Furthermore, the sensor analysis component 132 may protect patient privacy when sensor data used to determine whether the patient is moving or attempting to move towards the patient relief device 102 includes images, video, audio data, and the like. In some examples, the sensor analysis component 132 may be at least partially included in a device with a camera, and may cause the camera to capture images or video which may be used by the sensor analysis component 132 to determine whether the patient is moving or attempting to move towards the patient relief device 102. In such cases, the sensor analysis component 132 may generate the sensor data to indicate a change in a location of the patient without a processor of the device transmitting the image or the video to other devices, including the clinician device 104. For example, the sensor analysis component 132 may transmit a message to be displayed by the clinician device 104 such as "Check on Patient for Toileting Need" rather than transmitting the image or video itself. Alternatively or additionally, the sensor analysis component 132 may transmit a signal to a light outside of the patient's hospital room door that changes the color of the light to indicate that assistance is needed inside of the room. Other examples are also considered.

In some cases, the sensor analysis component 132 may be located remotely from a camera (e.g., at a server or the clinician device 104), and may receive images or video which may be used to determine whether the patient is moving or attempting to move towards the patient relief device 102. In such cases, the sensor analysis component 132 may generate the sensor data to indicate a change in a location of the patient without a processor of the device providing the image or the video for display by the clinician device 104. Similar to the discussion above, the sensor analysis component 132 may cause a message to be displayed by the clinician device 104 such as "Check on Patient for Toileting Need" rather than displaying the image or video itself.

Whether or not the patient receives assistance moving to the patient relief device 102, the toilet event component 124 may notify a healthcare provider that the patient is using the patient relief device 102, and/or may notify a healthcare provider when the patient concludes using the patient relief device 102. By providing a notification to a healthcare provider of use and/or conclusion of use of the patient relief device 102 by the patient, the healthcare provider can anticipate whether the patient will need assistance upon conclusion of using the patient relief device 102. Accordingly, the healthcare provide may prevent accidents or falls that may occur when the patient returns to a bed or a chair from the patient relief device 102, may promptly clean following a toileting event to prevent infection or unsanitary conditions, and so forth.

In many examples, the sensor analysis component 132 may receive sensor data from the patient relief device 102, the clinician device 104, and/or the healthcare establishment device(s) 106, and determine, from the sensor data, that the patient is using the patient relief device 102. Further, the sensor analysis component 132 may receive sensor data from the patient relief device 102, the clinician device 104, and/or the healthcare establishment device(s) 106, and determine, from the sensor data, that the patient has concluded using the patient relief device 102. The notification component 134 may provide a notification to the clinician device 104 and/or a healthcare establishment device 106 indicating that the patient is using, or has concluded using, the patient relief device upon receiving sensor data indicating such. For example, the notification component 134 may send a notification to the clinician device 104 that includes a message such as "Patient Concluded with Toileting", and/or may change a color of a light outside of the patient's room from one color to a different color, indicating that assistance is needed inside of the bathroom to return the patient to a hospital bed.

Following are several non-limiting, illustrative examples of determining that the patient is using and/or has concluded using the patient relief device 102, and notifications indicating such. In some cases, the sensor analysis component 132 may receive sensor data from multiple sensors (e.g., according to the illustrative examples below or otherwise) and determine that the patient is using and/or has concluded using the patient relief device 102 based on the sensor data received from the different sensors.

In some examples, the sensor 112 may be a pressure sensor associated with a seat of the patient relief device 102. The sensor 112 may generate first sensor data which is transmitted to the sensor analysis component 132, where the sensor analysis component 132 may determine that a person (e.g., the patient) is sitting down on the seat of the patient relief device 102 based on an increase in pressure on the seat indicated by the sensor data. Additionally, in examples, the sensor 112 may generate second sensor data which is transmitted to the sensor analysis component 132, where the sensor analysis component 132 may determine that the patient is leaving or has left the seat of the patient relief device 102 based on a decrease in pressure on the seat indicated by the sensor data. Based on the sensor analysis component 132 determining that the patient is using and/or has concluded using the patient relief device 102, the notification component 134 may provide a notification to the clinician device 104 to check on the patient to see if the patient requires assistance.

In some cases, the sensor 112 may be a motion sensor included in a toilet paper roll in a bathroom associated with a hospital room of the patient. Motion of toilet paper on a toilet paper roll often indicates conclusion of a toileting event. Accordingly, if the sensor analysis component 132 receives sensor data from a motion sensor included in a toilet paper roll, the sensor analysis component 132 may deter-mine that the patient has concluded using the patient relief device 102. Based on the sensor analysis component 132 determining that the patient has concluded using the patient relief device 102, the notification component 134 may provide a notification to the clinician device 104 to check on the patient to see if the patient requires assistance.

In some examples, the sensor 112 may be a flush sensor associated with the patient relief device 102. Flushing of the patient relief device 102 often indicates conclusion of a toileting event. Accordingly, if the sensor analysis component 132 receives sensor data from a flush sensor of the patient relief device 102, the sensor analysis component 132 may determine that the patient has concluded using the patient relief device 102. Based on the sensor analysis component 132 determining that the patient has concluded using the patient relief device 102, the notification component 134 may provide a notification to the clinician device 104 to check on the patient to see if the patient requires assistance.

Audio data may also be used to determine whether the patient is using and/or has concluded using the patient relief device 102. For example, one or more microphones may be located in a hospital room, a bathroom, in the patient relief device 102, and/or in a healthcare establishment device 106 which may be used to collect audio data to determine whether the patient is using and/or has concluded using the patient relief device 102. The microphone may provide audio data to the sensor analysis component 132, and the sensor analysis component 132 may analyze the audio data to determine, for example, whether the patient is sitting down on the patient relief device 102. Additionally, the sensor analysis component 132 may analyze the audio data to determine whether the patient has left the patient relief device 102, whether the patient has flushed the patient relief device 102, whether the patient is washing their hands in a sink, and so forth, any of which may indicate that the patient has concluded using the patient relief device 102. Based on the sensor analysis component 132 determining that the patient is using and/or has concluded using the patient relief device 102, the notification component 134 may provide a notification to the clinician device 104 to check on the patient to see if the patient requires assistance.

In some examples, the sensor 112 may be a heartrate sensor configured to detect a heartrate of a person using the patient relief device 102, and/or a respiration sensor configured to detect respiration by a person using the patient relief device 102. For instance, a heartrate sensor or respiration sensor may be located in a seat of the patient relief device 102, such that when a person makes contact with the seat, the sensor 112 is able to detect heartrate or respiration. The sensor 112 may generate first sensor data which is transmitted to the sensor analysis component 132, where the sensor analysis component 132 may determine that a person (e.g., the patient) is sitting down on the seat of the patient relief device 102 based on a presence of a heartbeat and/or respiration indicated by the sensor data. Additionally, in examples, the sensor 112 may generate second sensor data which is transmitted to the sensor analysis component 132, where the sensor analysis component 132 may determine that the patient is leaving or has left the seat of the patient relief device 102 based on an absence of a heartbeat and/or respiration indicated by the sensor data. Based on the sensor analysis component 132 determining that the patient is using and/or has concluded using the patient relief device 102, the notification component 134 may provide a notification to the clinician device 104 to check on the patient to see if the patient requires assistance.

In addition to determining a presence and/or absence of a person based on heartrate or respiration detected by the sensor 112, the sensor analysis component 132 may determine whether a person using the patient relief device 102 is a patient or a different person based on the heartrate or respiration indicated by the sensor data. For example, upon receiving the sensor data from the sensor, the sensor analysis component 132 may determine a pattern associated with the heartrate detected by the heartrate sensor, or a pattern associated with the respiration detected by the respiration sensor. A pattern associated with heartrate may include a rate at which heartbeats are detected, arrythmias, and so forth. A pattern associated with respiration rate may include a rate at which breaths are detected, evidence of abnormal breathing patterns (e.g., orthopnea, dyspnea, hyper- or hypoventilation, etc.), and so on.

The sensor analysis component 132 may determine a similarity of the pattern indicated by the sensor data to a pattern associated with the patient in the EMR 118. For example, if the pattern indicated by the sensor data is greater than a threshold similarity (e.g., greater than 95%) to the pattern associated with the patient in the EMR 118, the sensor analysis component 132 may determine that the patient is using the patient relief device 102. In such cases when the patient is determined to be using the patient relief device 102, the notification component 134 may provide a notification to the clinician device 104 for assistance with the patient as described herein. If the pattern indicated by the sensor data is less than or equal to the threshold similarity of the pattern associated with the patient in the EMR 118, the sensor analysis component 132 may determine that a person other than the patient is using the patient relief device 102. In such cases when a person other than the patient is determined to be using the patient relief device 102, the notification component 134 may withhold sending a notification to the clinician device 104, to prevent unnecessary calls from being placed to healthcare providers.

In some cases, radar data may be used to determine whether the patient is using and/or has concluded using the patient relief device 102. For example, a radar detector may be located in a hospital room, a bathroom, in the patient relief device 102, and/or in a healthcare establishment device 106 which may be used to collect radar data to determine whether the patient is using and/or has concluded using the patient relief device 102. The radar detector may provide radar data to the sensor analysis component 132, and the sensor analysis component 132 may analyze the radar data to determine, for example, whether the patient is standing in front of or sitting down on the patient relief device 102. Additionally, the sensor analysis component 132 may analyze the radar data to determine whether the patient has left the patient relief device 102, which may indicate that the patient has concluded using the patient relief device 102. Based on the sensor analysis component 132 determining that the patient is using and/or has concluded using the patient relief device 102, the notification component 134 may provide a notification to the clinician device 104 to check on the patient to see if the patient requires assistance.

Additionally, in some examples, the sensor analysis component 132 may use images and/or video received from a camera in a hospital room (or bathroom) to determine whether the patient is using and/or has concluded using the patient relief device 102. For instance, the camera may provide images and/or video to the sensor analysis component 132, and the sensor analysis component 132 may analyze the images and/or video to determine, for example, whether the patient is standing in front of or sitting down on the patient relief device 102. Additionally, the sensor analysis component 132 may analyze the images and/or video to determine a change in a position of the patient relative to the patient relief device 102 (e.g., standing up, stepping away, moving to a wheelchair or other mobility assistance device, etc.), which may indicate that the patient has concluded using the patient relief device 102. Based on the sensor analysis component 132 determining that the patient is using and/or has concluded using the patient relief device 102, the notification component 134 may provide a notification to the clinician device 104 to check on the patient to see if the patient requires assistance.

Similar to the discussion above, the sensor analysis component 132 may control how images and/or video are stored, accessed, transferred, and displayed to maintain privacy of the patient. For instance, the sensor analysis component 132 may be part of a device that includes the camera. The sensor analysis component 132 may cause the camera of the device to capture images or video, and may use the images or video to determine a change in a position of the patient relative to the patient relief device 102, which may be indicative of the patient concluding use of the patient relief device 102. The sensor analysis component 132 may generate sensor data that indicates the change in position of the patient relative to the patient relief device 102 without transmitting the images or the video to a different device (e.g., the clinician device 104) where the images or video may be viewed on a display. The notification component 134 may output a notification that indicates that the patient has concluded using the patient relief device 102 based on the sensor data transmitted by the sensor analysis component 132, without the notification including the images or the video.

Alternatively or additionally, the sensor analysis component 132 may be included in a device that is remote from a camera, and the images or video may be transmitted to the sensor analysis component 132 from the camera. The sensor analysis component 132 may use the images or video to determine a change in a position of the patient relative to the patient relief device 102, which may be indicative of the patient concluding use of the patient relief device 102 as described above. The notification component 134 may output a notification that indicates that the patient has concluded using the patient relief device 102 without providing the images or video for display, such as by a display of the clinician device 104. In this way, the privacy of the patient is maintained, while enabling healthcare providers to provide assistance with toileting when needed.

In some examples, the notification component 134 may identify a risk associated with the patient, and generate the notification to be provided to the clinician device 104 that indicates the risk. For instance, the notification component 134 may determine a condition of the patient included in the EMR 118, such as mobility of the patient, whether the patient is likely to fall and/or is likely to sustain an injury if the patient falls (e.g., due to age, decreased bone density, etc.), medications that have been administered to the patient (e.g., medications that may affect balance or increase risk of falling), and so forth. If the notification component 134 determines that a condition of the patient included in the EMR 118 may require additional time and/or assistance to assist the patient with accessing the patient relief device 102, the notification component 134 may generate the notification to include such information, and/or may provide the notification at a time to account for the assistance required by the patient.

In an illustrative example, the EMR 118 of a patient may indicate that the patient has limited mobility, and requires the use of a lift and two healthcare providers to move from a hospital bed to the patient relief device 102 based on the patient's limited mobility. Accordingly, the notification component 134 may generate a notification that includes a message such as "Patient Toileting Need Detected—Lift and 2 Personnel Needed." The notification component 134 may provide the message to two clinician devices 104 associated with two healthcare providers to notify the healthcare providers that assistance is required for the patient to access the patient relief device 102. In some cases, the notification component 134 may prioritize the notification as urgent when providing the notification to the clinician devices 104, so that the healthcare providers allot sufficient time to transfer the patient to the patient relief device 102 using the lift and to account for the patient's limited mobility. For instance, the notification component 134 may prioritize the notification by listing a task associated with the toileting need ahead of a task to deliver a meal to a different patient, and/or may cause an alert (e.g., an audio alert, a haptic alert, etc.) to be output by the clinician device 104.

Alternatively or additionally, the notification component 134 may receive information from one or more of the healthcare establishment devices 106 indicating a risk associated with a hospital room and/or bathroom that the patient may encounter when using the patient relief device 102. Risks in a hospital room and/or bathroom may include a wet or slick floor, cords or tubes that may trip the patient on the way to the patient relief device 102, objects or furniture that may be in the way of the patient accessing the patient relief device 102, and so on. In many cases, a camera may provide the notification component 134 with an image or a video, where the notification component 134 may determine the risk from the image or the video using computer vision (e.g., a neural network). Examples are also considered in which a sensor in a floor detects pressure and/or moisture on the floor, and provides sensor data indicating the pressure or moisture to the notification component 134. The notification component 134 may determine a risk based on the sensor data provided by the moisture sensor or pressure sensor located in the floor. The notification component 134 may include an indication of the risk in the notification provided to the clinician device 104, so that a healthcare provider may provide assistance to mitigate the risk when the patient is traveling to or from the patient relief device 102.

Figure 5:
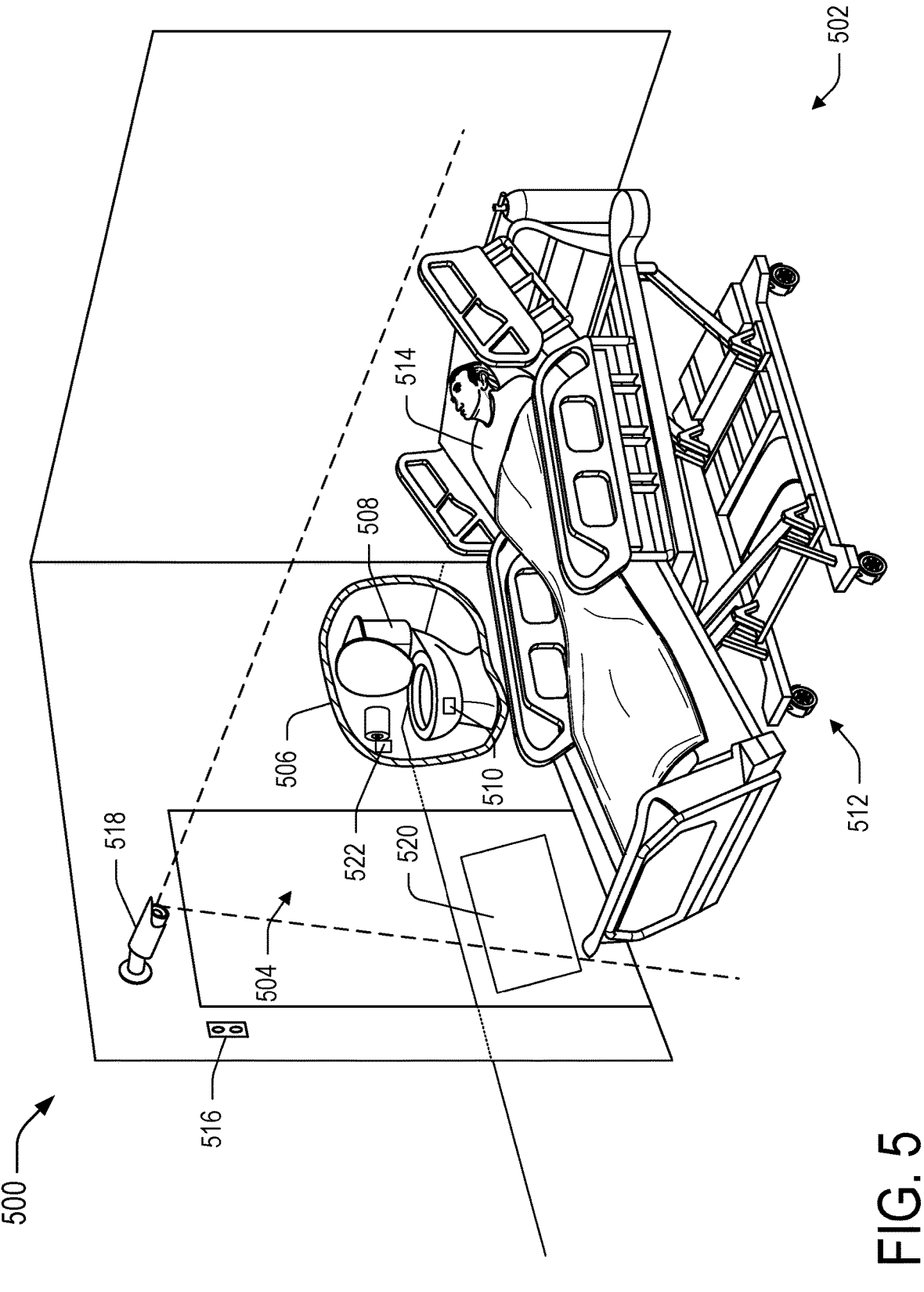
FIG. 5 is an example environment including devices that may be used to provide advance notice of toileting events, in accordance with examples of the disclosure.

FIG. 5 is an example environment 500 including devices that may be used to provide advance notice of toileting events, in accordance with examples of the disclosure. The example environment 500 includes a hospital room 502 and a bathroom 504 proximate the hospital room 502. A cutaway 506 shows a patient relief device 508 inside of the bathroom 504, where the patient relief device 508 may provide the same or similar functionality to the patient relief device 102 of FIG. 1. For example, the patient relief device 508 may include one or more sensors 510, which may provide the same or similar functionality as the sensors 112 described in relation to FIG. 1. Additionally, the hospital room 502 includes a hospital bed 512, which is shown being used by a patient 514.

Various sensors included in the hospital room 502 and/or the bathroom 504 may provide the sensor analysis component 132 of FIG. 1 with sensor data, which the sensor analysis component 132 may use to determine whether the patient 514 is moving or attempting to move towards the patient relief device 508, determine whether the patient 514 is using the patient relief device 508, and/or determine whether the patient 514 has concluded using the patient relief device 508. For example, a pressure sensor or motion sensor (not pictured) associated with the hospital bed 512 may detect movement by the patient 514 in the hospital bed 512. Movement by the patient 514 in the hospital bed 512 may indicate that the patient 514 is attempting to move towards the patient relief device 508. If the sensor analysis component 132 determines that the patient 514 is attempting to move towards the patient relief device 508 based on sensor data provided by a sensor associated with the hospital bed 512, the notification component 134 of FIG. 1 may provide a notification to a healthcare provider indicating such. In some cases, the notification component 134 may provide the notification to the clinician device 104 of FIG. 1 as described herein.

Alternatively or additionally, the notification component 134 may provide a signal to a healthcare establishment device 516 that indicates to a healthcare provider that the patient is attempting to move towards the patient relief device 508. In the illustrated example, the healthcare establishment device 516 is a light fixture configured to emit light from two different bulbs, although any light fixture configuration is considered without departing from the scope of this disclosure. Additionally, the healthcare establishment device 516 is shown inside of the hospital room 502 for clarity, but examples are considered in which the healthcare establishment device 516 is located outside of the hospital room 502 (e.g., in a hallway proximate the hospital room), at a nurse's station, and the like. The notification component 134 may provide the signal to the healthcare establishment device 516 which may cause a color of a light to be emitted that indicates that the patient may need assistance.

In some examples, the hospital room 502 may also include a camera 518 configured to capture images and/or video of the hospital room 502, and provide the images and/or video to the sensor analysis component 132. In some cases, the sensor analysis component 132 may analyze the images and/or video to determine a change in a position and/or location of the patient 514. A change in position or location of the patient 514 may indicate that the patient 514 is moving or attempting to move toward the patient relief device 508. For example, if the patient 514 sits up in the hospital bed 512, moves to a side of the hospital bed 512, begins "tossing and turning" in the hospital bed 512, or the like, the sensor analysis component 132 may determine from images or video of such movement by the patient 514 that the patient 514 may be moving or attempting to move towards the patient relief device 508. Based on a determination by the sensor analysis component 132 that the patient 514 is moving or attempting to move towards the patient relief device 508 using images and/or video provided by the camera 518, the notification component 134 may provide a notification to the clinician device 104 and/or the healthcare establishment device 516 indicating that the patient may need assistance. While generally described as a camera configured to capture images or video, the camera 518 may be associated with a different sensor type and configured to capture other sensor data types as well, such as infrared data, radar data, audio data, and so forth as described herein.

The bathroom 504 (and in some cases the hospital room 502, although not explicitly pictured) may include a sensor 520 on a floor that is configured to sense pressure applied to the floor. The sensor 520 may provide sensor data to the sensor analysis component 132 indicating a pressure applied to the sensor 520. In some cases, the sensor analysis component 132 may analyze the sensor data provided by the sensor 520 to determine a location of the patient 514. In some examples, the sensor 520 may be placed in a location relative to the patient relief device 508 such that stepping or moving on the sensor 520 may indicate that the patient 514 (or another person) is moving or attempting to move toward the patient relief device 508. Based on a determination by the sensor analysis component 132 that the patient 514 is moving or attempting to move towards the patient relief device 508 using sensor data provided by the sensor 520, the notification component 134 may provide a notification to the clinician device 104 and/or the healthcare establishment device 516 indicating that the patient may need assistance. While generally described as a pressure sensor configured to sense pressure applied to the floor, the sensor 520 may be associated with a different sensor type and configured to capture other sensor data types as well, such as moisture data, temperature data, and the like. For instance, as described herein, detection of moisture on the floor using the sensor 520 may indicate a risk to the patient 514 when moving towards the patient relief device 508, and the notification provided by the notification component 134 may indicate the risk to the healthcare provider that is providing assistance to the patient 514.

The sensors included in the hospital room 502 and/or bathroom 504 may provide the sensor analysis component 132 with sensor data which the sensor analysis component 132 may use to determine if the patient 514 is using the patient relief device 508 as well. For example, the sensor 520 may be positioned on the floor proximate the patient relief device 508 such that sensor data provided by the sensor 520 may indicate whether the patient 514 is standing at the patient relief device 508 and/or sitting at the patient relief device 508 for a toileting event, based on pressure applied to the sensor 520. Similarly, the camera 518 may be positioned in the bathroom 504 such that images and/or video provided by the camera 518 may indicate whether the patient 514 is standing at the patient relief device 508 and/or sitting at the patient relief device 508 for a toileting event. As described above, the camera 518 may output sensor data indicative of whether the patient 514 is using the patient relief device 508 without providing images or video of the patient using the patient relief device 508 to protect privacy of the patient.

Additionally, in some examples, the patient relief device 508 may include the sensors 510 which may be configured to provide sensor data to the sensor analysis component 132, where the sensor analysis component 132 can analyze the sensor data to determine whether the patient 514 is using the patient relief device 508. For instance, the sensors 510 may include a pressure sensor associated with a seat of the patient relief device 508, a heartrate sensor associated with a seat of the patient relief device 508, a respiration sensor associated with a seat of the patient relief device 508, a motion sensor associated with the patient relief device 508, a light beam sensor associated with the patient relief device 508, a liquid volume sensor associated with the patient relief device 102, and so forth. In some cases, based on determining that the patient 514 is using the patient relief device 508, the notification component 134 may provide a notification to the clinician device 104 and/or the healthcare establishment device 516 indicating that the patient is using the patient relief device 508. Therefore, healthcare providers may anticipate needs of the patient that may follow a toileting event, such as resetting mobility devices, accessing cleaning products, and the like.

Furthermore, the sensors included in the hospital room 502 and/or the bathroom 504 may provide the sensor analysis component 132 with sensor data which the sensor analysis component 132 may use to determine if the patient 514 has concluded using the patient relief device 508. As described above, the sensor 520 may be positioned on the floor proximate the patient relief device 508 such that sensor data provided by the sensor 520 indicates whether the patient 514 is standing at the patient relief device 508 and/or sitting at the patient relief device 508 for a toileting event, based on pressure applied to the sensor 520. If the sensor 520 detects a reduction in pressure, the sensor analysis component 132 may determine that the patient 514 has moved away from the patient relief device 508, and thus has concluded using the patient relief device 508.

Also as described above, the camera 518 may be positioned in the bathroom 504 such that images and/or video provided by the camera 518 may indicate whether the patient 514 is standing at the patient relief device 508 and/or sitting at the patient relief device 508 for a toileting event. If an image or video provided by the camera 518 indicates a change in a location or position of the patient 514 relative to the patient relief device 508 from the images or video, the sensor analysis component 132 may determine that the patient has concluded using the patient relief device 508. Similar to the discussion above, the camera 518 may output sensor data indicative of the patient 514 concluding use of the patient relief device 508 without providing images or video of the patient to another device to protect privacy of the patient.

In examples, the sensors 510 of the patient relief device 508 may provide sensor data to the sensor analysis component 132, where the sensor analysis component 132 can analyze the sensor data to determine whether the patient 514 has concluded using the patient relief device 508. For example, a change in pressure by a pressure sensor associated with a seat of the patient relief device 508 may indicate that the patient 514 has concluded using the patient relief device 508. In another example, motion detected by a motion sensor associated with the patient relief device 508 may indicate that the patient 514 has concluded using the patient relief device 508. Other examples that may indicate that the patient 514 has concluded using the patient relief device 508 may include resuming detection of a light beam by a light beam sensor, detection of an absence of a heartrate by a heartrate sensor, detection of an absence of respiration by a respiration sensor, detection of a change in volume of liquid by a liquid volume sensor, detecting a flush by a flush sensor, and so on. Additionally, the bathroom 504 may include a motion sensor 522 associated with a toilet paper roll, which may provide sensor data to the sensor analysis component 132, which the sensor analysis component 132 may use to determine that the patient 514 has concluded using the patient relief device 508. In some cases, based on determining that the patient 514 has concluded using the patient relief device 508, the notification component 134 may provide a notification to the clinician device 104 and/or the healthcare establishment device 516 indicating that the patient has concluded using the patient relief device 508.

Example environment 500 may also include an IV pump (not shown) that may deliver fluids, such as nutrients and medications, into a patient's body in controlled amounts. As described above, use of an IV pump with certain nutrients or medications may cause an override rule to be control the toilet need schedule of a patient. For example, an IV pump may administer a Lasix drip at 10 mg/hr for 24 hours, or a normal saline bolus of 1000 ml ×1. As such, use of an IV pump may affect when a clinician or healthcare provider is notified of an expected toileting need of a patient.

FIG. 6 is an example process 600 for providing advance notice of toileting events, according to the techniques described herein. In some examples, one or more operations of the process 600 may be combined with one or more operations of the method illustrated in FIG. 4. In some examples, the process 600 may be performed by one or more processors of computing devices, such as the patient management system 108 of FIG. 1.

At operation 602, the toilet event component 124 receives, from a sensing device associated with a patient relief device, first sensor data. In some examples, the sensor analysis component 132 of the toilet event component 124 may receive first sensor data from one or more sensors associated with the patient relief device 102, the clinician device 104, and/or the healthcare establishment device 106. For instance, the sensor analysis component 132 may receive the first sensor data from the one or more sensors 112 associated with the patient relief device 102, such as a pressure sensor associated with a seat of the patient relief device 102, a heartrate sensor associated with a seat of the patient relief device 102, a respiration sensor associated with a seat of the patient relief device 102, a motion sensor associated with the patient relief device 102, a flush sensor associated with the patient relief device 102, a light beam sensor associated with the patient relief device 102, a liquid volume sensor associated with the patient relief device 102, and so forth. Alternatively or additionally, the sensor analysis component 122 may receive sensor data from one or more sensors from the healthcare establishment device(s) 106, such as a pressure sensor (e.g., included in a hospital bed, a chair, the floor, etc.), a light beam sensor that senses interruptions of a light beam when objects pass through the light beam, a real time location sensor (RTLS) (e.g., included in a gown, a sock, a bracelet, an incontinence device, etc.) worn by the patient, a motion sensor, a radar sensor, a camera, a microphone, and so on. In some cases, the sensor analysis component 122 may receive data from the clinician device 104, such as inputs by a healthcare provider related to toileting events, data from a RTLS sensor, data from a motion sensor, and the like.

At operation 604, the toilet event component 124 determines whether the patient is using the patient relief device. For example, the sensor analysis component 132 may determine the presence or absence of a person sitting at and/or standing near the patient relief device 102 based on the first sensor data, as described herein. Additionally, in some examples, the sensor analysis component 132 may determine whether a person using the patient relief device is the patient or a different person, such as using facial recognition of an image or video at a time prior to and/or during a toileting event, based on a heartrate pattern detected by the sensor 112, based on a respiration pattern detected by the sensor 112, and so forth.

If the toilet event component 124 determines that the patient is not using the patient relief device (e.g., "No" at operation 604), the process 600 may return to the operation 602 and continue receiving the first sensor data. In some cases, the sensor analysis component 132 may continue monitoring the first sensor data until the patient is detected to be using the patient relief device 102.

If the toilet event component 124 determines that the patient is using the patient relief device (e.g., "Yes" at operation 604), the process 600 may proceed to operation 606, in which the toilet event component 124 receives second sensor data from the sensing device associated with the patient relief device. For instance, the sensor analysis component 132 may continue monitoring the second sensor data until a change in a location of the patient and/or a change in a position of the patient is determined from the second sensor data. This may include determining the presence or absence of the patient at the patient relief device 102, such as by detecting the presence or absence of a heartrate or respiration signal, or determining a change in pressure applied to a seat of the patient relief device 102. Alternatively or additionally, the second sensor data may be associated with a conclusion of a toileting event, such as sensor data received from a motion sensor associated with a toilet paper roll, a flush sensor, and the like. Accordingly, at operation 608, the toilet event component 124 determines whether the patient has concluded using the patient relief device.

If the toilet event component 124 determines that the patient has not concluded using the patient relief device (e.g., "No" at operation 608), the process 600 may return to the operation 606 and continue receiving the second sensor data. However, if the toilet event component 124 determines that the patient has concluded using the patient relief device (e.g., "Yes" at operation 608), the process 600 may proceed to operation 610, in which the toilet event component 124 provides a notification to a device associated with a healthcare provider, where the notification indicates that the patient has concluded using the patient relief device. The notification component 134 of the toilet event component 124 may provide the notification to one or more clinician devices 104 based on an amount of assistance required by the patient to conclude using the patient relief device 102 and/or to return to a hospital bed or chair from the patient relief device 102. Alternatively or additionally, the notification component 134 may provide a signal to a healthcare establishment device 106 that indicates to a healthcare provider the conclusion of the toileting event by the patient, such as by changing a color of a light outside of a door to the bathroom or hospital room of the patient to indicate that the patient may need assistance.

Example System and Device

Figure 7:
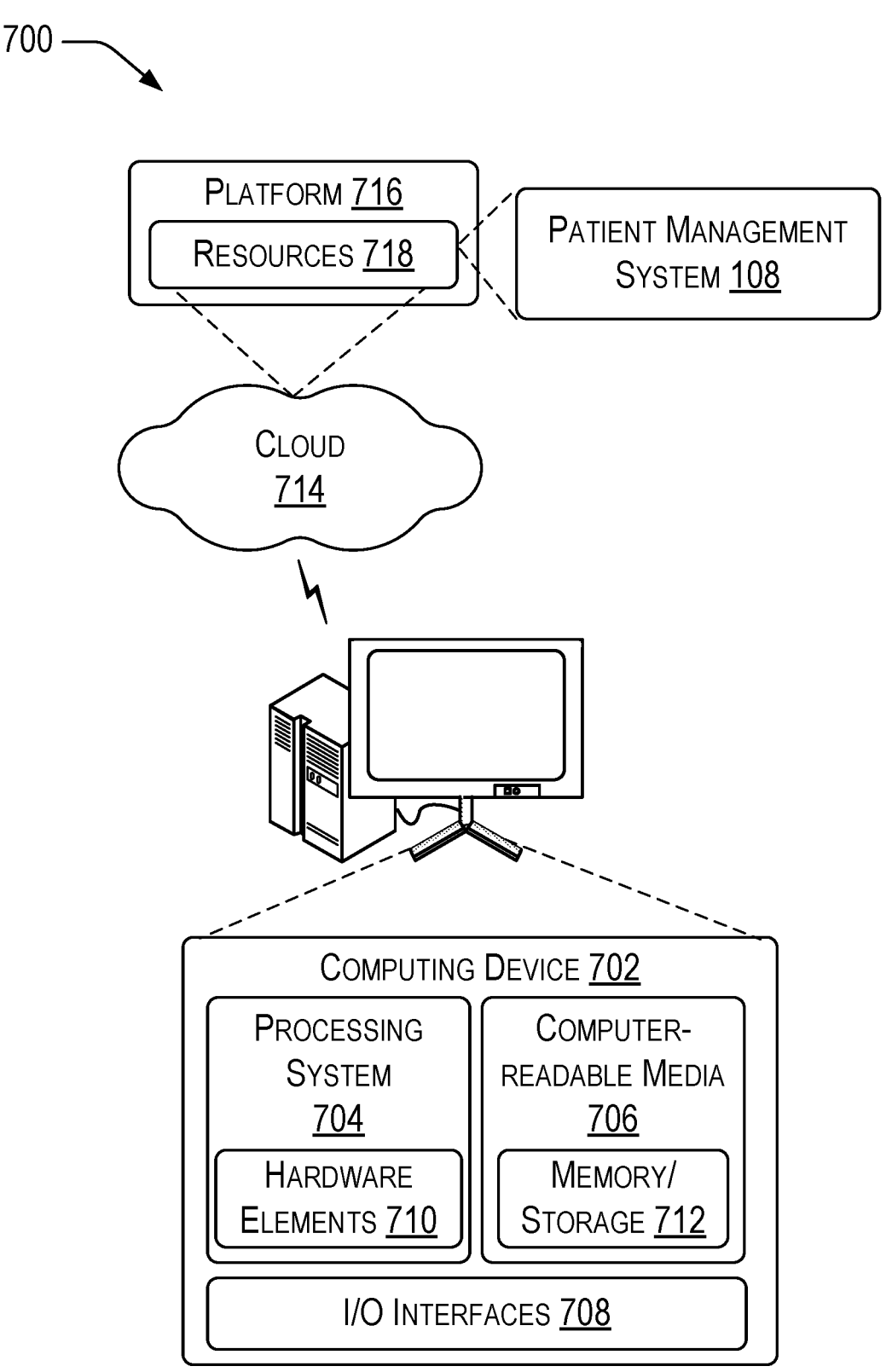
FIG. 7 depicts an example computing system and device which may be used to implement the described techniques.

FIG. 7 illustrates an example system generally at 700 that includes an example computing device 702 that is representative of one or more computing systems and/or devices that may implement the various techniques described herein. This is illustrated through inclusion of the patient management system 108. The computing device 702 may be, for example, a server of a service provider, a device associated with a client (e.g., a client device), an on-chip system, and/or any other suitable computing device or computing system.

The example computing device 702 as illustrated includes a processing system 704, one or more computer-readable media 706, and one or more I/O interface 708 that are communicatively coupled, one to another. Although not shown, the computing device 702 may further include a system bus or other data and command transfer system that couples the various components, one to another. A system bus can include any one or combination of different bus structures, such as a memory bus or memory controller, a peripheral bus, a universal serial bus, and/or a processor or local bus that utilizes any of a variety of bus architectures. A variety of other examples are also contemplated, such as control and data lines.

The processing system 704 is representative of functionality to perform one or more operations using hardware. Accordingly, the processing system 704 is illustrated as including hardware element 710 that may be configured as processors, functional blocks, and so forth. This may include implementation in hardware as an application specific integrated circuit or other logic device formed using one or more semiconductors. The hardware elements 710 are not limited by the materials from which they are formed or the processing mechanisms employed therein. For example, processors may be comprised of semiconductor(s) and/or transistors (e.g., electronic integrated circuits (ICs)). In such a context, processor-executable instructions may be electronically-executable instructions.

The computer-readable media 706 is illustrated as including a memory/storage component 712. The memory/storage component 712 represents memory/storage capacity associated with one or more computer-readable media. The memory/storage component 712 may include volatile media (such as random access memory (RAM)) and/or nonvolatile media (such as read only memory (ROM), Flash memory, optical disks, magnetic disks, and so forth). The memory/storage component 712 may include fixed media (e.g., RAM, ROM, a fixed hard drive, and so on) as well as removable media (e.g., Flash memory, a removable hard drive, an optical disc, and so forth). The computer-readable media 706 may be configured in a variety of other ways as further described below.

Input/output interface(s) 708 are representative of functionality to allow a user to enter commands and information to computing device 702, and also allow information to be presented to the user and/or other components or devices using various input/output devices. Examples of input devices include a keyboard, a cursor control device (e.g., a mouse), a microphone, a scanner, touch functionality (e.g., capacitive or other sensors that are configured to detect physical touch), a camera (e.g., which may employ visible or non-visible wavelengths such as infrared frequencies to recognize movement as gestures that do not involve touch), and so forth. Examples of output devices include a display device (e.g., a monitor or projector), speakers, a printer, a network card, tactile-response device, and so forth. Thus, the computing device 702 may be configured in a variety of ways as further described below to support user interaction.

Various techniques may be described herein in the general context of software, hardware elements, or program modules. Generally, such modules include routines, programs, objects, elements, components, data structures, and so forth that perform particular tasks or implement particular abstract data types. The terms "module," "functionality," "logic," and "component" as used herein generally represent software, firmware, hardware, or a combination thereof. The features of the techniques described herein are platform-independent, meaning that the techniques may be implemented on a variety of commercial computing platforms having a variety of processors.

An implementation of the described modules and techniques may be stored on and/or transmitted across some form of computer-readable media. The computer-readable media may include a variety of media that may be accessed by the computing device 702. By way of example, and not limitation, computer-readable media may include "computer-readable storage media" and "computer-readable transmission media."

"Computer-readable storage media" may refer to media and/or devices that enable persistent and/or non-transitory storage of information in contrast to mere signal transmission, carrier waves, or signals per se. Thus, computer-readable storage media refers to non-signal bearing media. The computer-readable storage media includes hardware such as volatile and non-volatile, removable and non-removable media and/or storage devices implemented in a method or technology suitable for storage of information such as computer-readable instructions, data structures, program modules, logic elements/circuits, or other data. Examples of computer-readable storage media may include, but are not limited to, RAM, ROM, EEPROM, flash memory or other memory technology, CD-ROM, digital versatile disks (DVD) or other optical storage, hard disks, magnetic cassettes, magnetic tape, magnetic disk storage or other magnetic storage devices, or other storage device, tangible media, or article of manufacture suitable to store the desired information and which may be accessed by a computer.

"Computer-readable transmission media" may refer to a medium that is configured to transmit instructions to the hardware of the computing device 702, such as via a network. Computer-readable transmission media typically may transmit computer-readable instructions, data structures, program modules, or other data in a modulated data signal, such as carrier waves, data signals, or other transport mechanism. Computer-readable transmission media also include any information delivery media. The term "modulated data signal" means a signal that has one or more of its characteristics set or changed in such a manner as to encode information in the signal. By way of example, and not limitation, computer-readable transmission media include wired media such as a wired network or direct-wired connection, and wireless media such as acoustic, radio frequency (RF), infrared, and other wireless media.

As previously described, hardware elements 710 and computer-readable media 706 are representative of modules, programmable device logic and/or device logic implemented in a hardware form that may be employed in some examples to implement at least some aspects of the techniques described herein, such as to perform one or more instructions. Hardware may include components of an integrated circuit or on-chip system, an application-specific integrated circuit (ASIC), a field-programmable gate array (FPGA), a complex programmable logic device (CPLD), and other implementations in silicon or other hardware. In this context, hardware may operate as a processing device that performs program tasks defined by instructions and/or logic embodied by the hardware as well as a hardware utilized to store instructions for execution, e.g., the computer-readable storage media described previously.

Combinations of the foregoing may also be employed to implement various techniques described herein. Accordingly, software, hardware, or executable modules may be implemented as one or more instructions and/or logic embodied on some form of computer-readable storage media and/or by one or more hardware elements 710. The computing device 702 may be configured to implement particular instructions and/or functions corresponding to the software and/or hardware modules. Accordingly, implementation of a module that is executable by the computing device 702 as software may be achieved at least partially in hardware, e.g., through use of computer-readable storage media and/or hardware elements 710 of the processing system 704. The instructions and/or functions may be executable/operable by one or more articles of manufacture (for example, one or more computing devices 702 and/or processing systems 704) to implement techniques, modules, and examples described herein.

The techniques described herein may be supported by various configurations of the computing device 702 and are not limited to the specific examples of the techniques described herein. This functionality may also be implemented all or in part through use of a distributed system, such as over a "cloud" 714 via a platform 716 as described below.

The cloud 714 includes and/or is representative of a platform 716 for resources 718. The platform 716 abstracts underlying functionality of hardware (e.g., servers) and software resources of the cloud 714. The resources 718 may include applications and/or data that can be utilized while computer processing is executed on servers that are remote from the computing device 702. Resources 718 can also include services provided over the Internet and/or through a subscriber network, such as a cellular or Wi-Fi network.

The platform 716 may abstract resources and functions to connect the computing device 702 with other computing devices. The platform 716 may also be scalable to provide a corresponding level of scale to encountered demand for the resources 718 that are implemented via the platform 716. Accordingly, in an interconnected device example, implementation of functionality described herein may be distributed throughout multiple devices of the system 700. For example, the functionality may be implemented in part on the computing device 702 as well as via the platform 716 which may represent a cloud computing environment, such as the cloud 714.

The example systems and methods of the present disclosure overcome various deficiencies of known prior art devices. Other examples of the present disclosure will be apparent to those skilled in the art from consideration of the specification and practice of the disclosure contained herein. It is intended that the specification and examples be considered as example only, with a true scope and spirit of the present disclosure being indicated by the following claims.

What is claimed is:

1. A system, comprising:

one or more processors;

a first electronic device in communication with the one or more processors via a network; and one or more computer-readable media storing instructions that, when executed by the one or more processors, cause the one or more processors to perform operations comprising:

receiving information indicating a condition associated with a patient;

receiving, from the first electronic device, an indication of an event associated with the patient;

determining, by a machine-learned model:

a first toilet need schedule for the patient based at least in part on the condition and the event, the first toilet need schedule corresponding to a first time period at which to check a toilet need of the patient; and a second toilet need schedule for the patient based at least in part on the condition and the event, the second toilet need schedule corresponding to a second time period greater than the first time period; and providing, to a second electronic device in communication with the one or more processors via the network, a notification associated with the first toilet need schedule, the notification indicating a prediction of a toilet need of the patient.

2. The system of claim 1, wherein the condition comprises at least one of:

a medication administered to the patient that affects a frequency of urine output or bowel movements;

an intravenous (IV) fluid dosage administered to the patient;

a disease of the patient;

a pregnancy of the patient;

a demographic of the patient;

an age of the patient;

a body mass index (BMI) of the patient;

a first presence of a catheter on the patient;

a second presence of an incontinence management device;

a colostomy or an ostomy on the patient; or a mobility of the patient.

3. The system of claim 1, wherein:

the condition is associated with a presence of a catheter on the patient, the first toilet need schedule comprises one or more catheter removal reminders, and the event is associated with removal of the catheter.

4. The system of claim 1, the operations further comprising:

receiving, by the one or more processors, information indicating one or more preferences of the patient associated with toileting events; and determining, by the machine-learned model, the first toilet need schedule based at least in part on the one or more preferences.

5. The system of claim 1, wherein the event comprises at least one of:

a meal eaten by the patient;

a feeding administered to the patient via a feeding tube;

a beverage consumed by the patient;

a medication administered to the patient; and an instance of a toileting event by the patient.

6. The system of claim 1, wherein:

the event comprises a meal eaten by the patient or a beverage consumed by the patient, and the second toilet need schedule corresponding to the second time period at which to check a toilet need of the patient.

7. The system of claim 1, wherein:

the event comprises an instance of a toileting event by the patient, and the second toilet need schedule corresponding to the second time period at which to check a toilet need of the patient.

8. The system of claim 7, wherein the indication of the event includes a measurement of a void associated with the toileting event, and wherein the second time period is based at least in part on a value representing the measurement.

9. A method, comprising:

training a machine-learned model, using one or more sets of training data, to identify relationships between patient conditions and patient preferences;

receiving, by a processor, information indicating a condition associated with a patient;

receiving, by the processor, information indicating one or more preferences of the patient associated with toileting events;

receiving, by the processor and from a second electronic device, an indication of an event associated with the patient, wherein the indication of the event comprises administration of a medication to the patient that affects a frequency of urine output or bowel movements;

determining, by the trained machine-learned model, a first toilet need schedule for the patient based at least in part on the condition and the one or more preferences, the first toilet need schedule corresponding to a time period;

providing, by the processor and to a third electronic device, a notification associated with the first toilet need schedule, the notification indicating a prediction of a toilet need of the patient; and determining, by the trained machine-learned model, a second toilet need schedule for the patient based at least in part on the condition, the one or more preferences, and the event, the second toilet need schedule corresponding to the time period and being different than the first toilet need schedule wherein the second toilet need schedule is based at least in part on a rule corresponding to toileting times associated with the medication that overrides the first toilet need schedule based on the prediction received from the machine-learned model.

10. The method of claim 9, wherein the one or more preferences of the patient associated with toileting events is indicative of an urgency with which the patient conducts the toileting events or a frequency with which the patient conducts the toileting events.

11. The method of claim 9, wherein the first toilet need schedule determined by the trained machine-learned model includes a prediction of a time at which the patient will experience a toileting need.

12. The method of claim 9, wherein the trained machine-learned model comprises one or more of a regression model, a neural network, or a gradient boost model, and wherein the trained machine-learned model is configured to provide the prediction customized to the patient and based on the condition.

13. The method of claim 9, further comprising:

inputting a parameter into the trained machine-learned model, the parameter associated with one or more of a healthcare provider or a healthcare establishment; and receiving, from the trained machine-learned model, a time at which to direct the healthcare provider to assist the patient with a toileting need based at least in part on the parameter, wherein the first toilet need schedule is further based on the time at which to direct the healthcare provider to assist the patient with the toileting need.

14. The method of claim 9, wherein the second electronic device is associated with a type of healthcare provider that provides a type of treatment, the method further comprising:

determining, by the trained machine-learned model, a treatment to administer to the patient based at least in part on the second toilet need schedule, the treatment being the type of treatment provided by the healthcare provider, wherein the notification to the second device indicates the treatment of the treatment type provided by the healthcare provider.

15. A system, comprising:

a processor;

a first electronic device in communication with the processor via a network;

a first sensor, separate from the first electronic device, in communication with the processor;

a second sensor, separate from the first electronic device, in communication with the processor; and one or more computer-readable media storing instructions that, when executed by the processor, cause the processor to perform operations comprising:

receiving first information from the first electronic device, via the network, indicating a condition associated with a patient;

receiving second information from the first sensor indicating an event associated with the patient;

determining, by a machine-learned model, a first toilet need schedule for the patient based at least in part on the first information and the second information, the first toilet need schedule corresponding to a time period;

generating, based on the first toilet need schedule, a notification indicating a predicted toilet need of the patient;

providing the notification to a second electronic device via the network;

receiving third information from the second sensor;

determining, by the processor, that the third information is associated with a toilet event;

generating a second notification indicating the toilet event; and providing the second notification to a third electronic device via the network.

16. The system of claim 15, further comprising:

the second electronic device, wherein the second electronic device is associated with the patient;

receiving, from the second electronic device, one or more preferences of the patient; and training the machine-learned model, to identify relationships between the one or more preferences of the patient, the condition, the event, and the first toilet need schedule.

17. The system of claim 15, further comprising:

the second sensor, wherein the second sensor is a camera, wherein the third information comprises;

data comprising of images or video;

wherein:

determining that the third information is associated with a toilet event comprises determining that the third information indicates that the patient is moving toward a patient relief device;

the second notification indicates that the patient is moving toward a patient relief device; and providing the second notification to a third electronic device via the network.

18. The system of claim 17, further comprising:

the second sensor, wherein the second sensor senses moisture;

wherein:

determining that the third information is associated with the toilet event comprises determining that the third information indicates urination by the patient in a hospital bed;

the second notification indicates that the patient urinated in the hospital bed; and providing the second notification to a third electronic device via the network.

* * * * *